United States Patent
Bishop et al.

(10) Patent No.: US 10,633,420 B2
(45) Date of Patent: Apr. 28, 2020

(54) ANTIMICROBIAL PEPTIDES WITH WOUND HEALING ACTIVITY

(71) Applicant: George Mason Research Foundation, Inc., Fairfax, VA (US)

(72) Inventors: Barney Bishop, Annandale, VA (US); Monique van Hoek, Centreville, VA (US); Ezra Myung Chul Chung, North Potomac, MD (US)

(73) Assignee: GEORGE MASON RESEARCH FOUNDATION, INC., Fairfax, VA (US)

( * ) Notice: Subject to any disclaimer, the term of this patent is extended or adjusted under 35 U.S.C. 154(b) by 0 days.

(21) Appl. No.: 16/316,646

(22) PCT Filed: Jul. 27, 2017

(86) PCT No.: PCT/US2017/044161
§ 371 (c)(1),
(2) Date: Jan. 10, 2019

(87) PCT Pub. No.: WO2018/022875
PCT Pub. Date: Feb. 1, 2018

(65) Prior Publication Data
US 2019/0352337 A1 Nov. 21, 2019

Related U.S. Application Data

(60) Provisional application No. 62/367,238, filed on Jul. 27, 2016.

(51) Int. Cl.
C07K 7/08 (2006.01)
A61P 17/02 (2006.01)
A61P 31/04 (2006.01)
A61L 27/34 (2006.01)
A61L 27/54 (2006.01)
C07K 7/06 (2006.01)
A01N 63/10 (2020.01)
A61K 38/00 (2006.01)

(52) U.S. Cl.
CPC ............... *C07K 7/08* (2013.01); *A01N 63/10* (2020.01); *A61L 27/34* (2013.01); *A61L 27/54* (2013.01); *A61P 17/02* (2018.01); *A61P 31/04* (2018.01); *C07K 7/06* (2013.01); *A61K 38/00* (2013.01); *A61L 2300/25* (2013.01); *A61L 2300/404* (2013.01)

(58) Field of Classification Search
None
See application file for complete search history.

(56) References Cited

U.S. PATENT DOCUMENTS 9,849,189 B2   12/2017   Bishop et al.
10,174,081 B2   1/2019   Bishop et al.
2012/0149631 A1   6/2012   Delatour et al.

OTHER PUBLICATIONS

Merchant, Mark et al., 'Antibacterial activities of serum from the Komodo Dragon (*Varanus komodoensis*)', Microbiology Research, 2013, vol. 4, pp. 16-20.
Van Hoek, Monique L., 'Antimicrobial peptides in reptiles', Pharmaceuticals, Jun. 10, 2014, vol. 7, pp. 723-753.
Juba, Melanie L. et al., 'Large scale discovery and de novo-assisted sequencing of cationic antimicrobial peptides (CAMPs) by microparticle capture and electron-transfer dissociation (ETD) mass spectrometry', Journal of Proteome Research, Sep. 1, 2015, vol. 14, pp. 4282-4295.
Montgomery, Joel M. et al., 'Aerobic salivary bacteria in wild and captive Komodo dragons', Journal of Wildlife Diseases, 2002, vol. 38, Issue 3, pp. 545-551.
Chung, Ezra M.C. et al., 'Komodo dragon-inspired synthetic peptide DRGN-1 promotes wound-healing of a mixed-biofilm infected wound', npj Biofilms and Microbiomes, Apr. 11, 2017(online), vol. 3, Article No. 9, internal pp. 1-13.
International Search Report (Form PCT/ISA/210) dated Nov. 7, 2017 in PCT/US2017/044161.

*Primary Examiner* — Lianko G Garyu
(74) *Attorney, Agent, or Firm* — Birch, Stewart, Kolasch & Birch, LLP

(57) ABSTRACT

Peptides having antimicrobial properties are described herein, as are compositions containing such peptides, and methods for using the peptides.

20 Claims, 12 Drawing Sheets

Specification includes a Sequence Listing.

SPKKTKPVKPKKVA (SEQ ID NO:1)
MS data of VK25/sequence with MS assignment

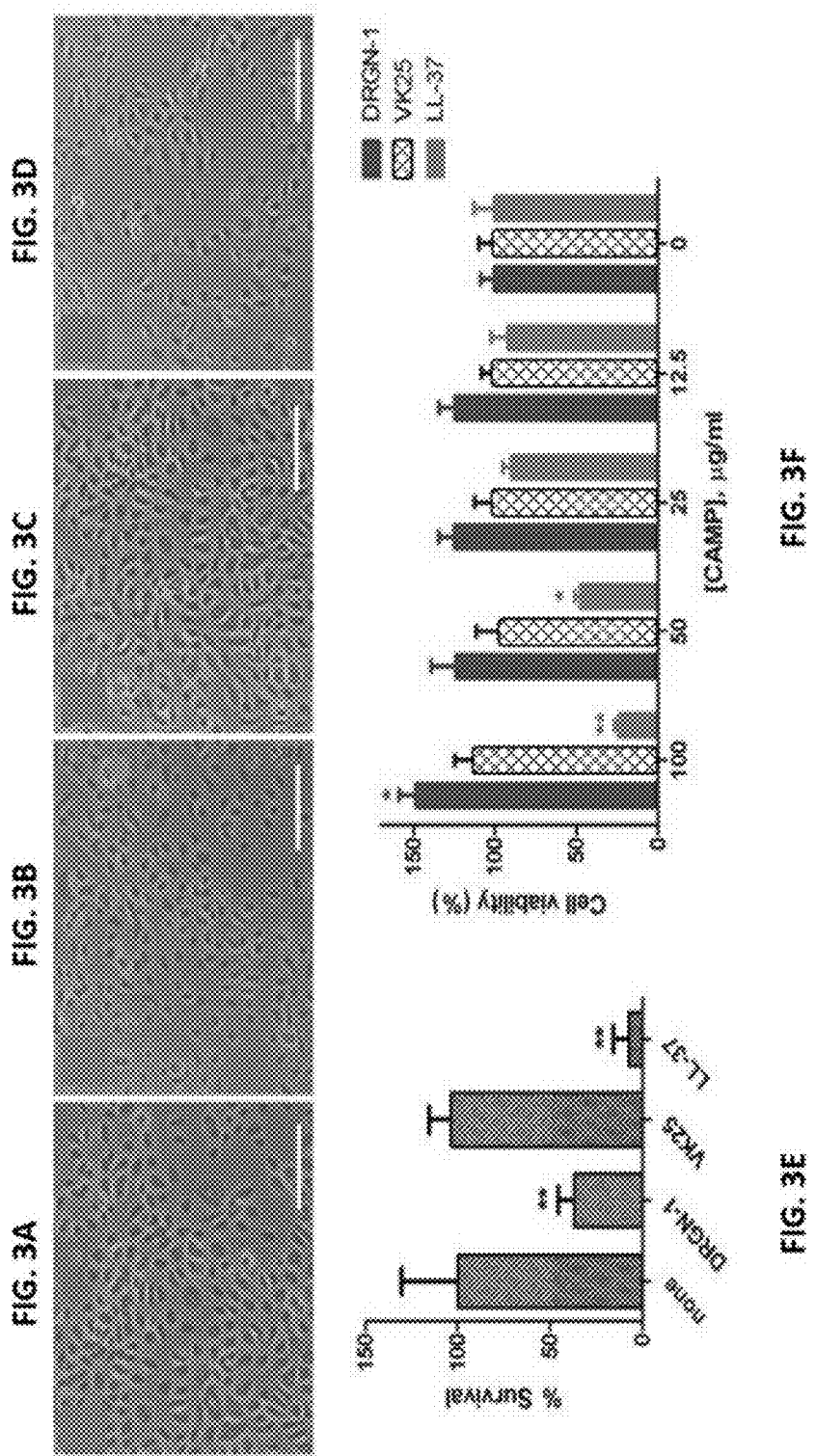

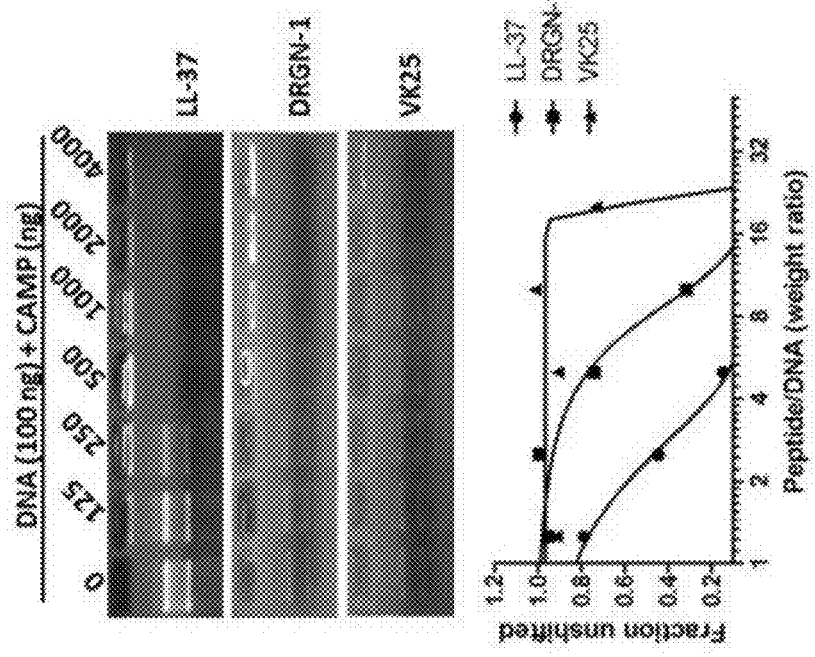
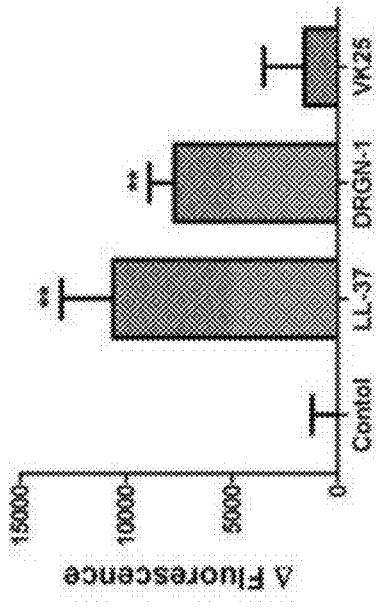
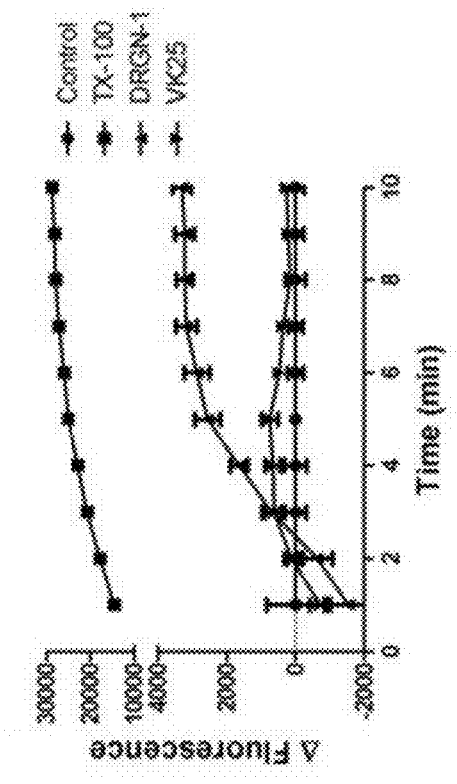
FIG. 5A
FIG. 5B
FIG. 5C

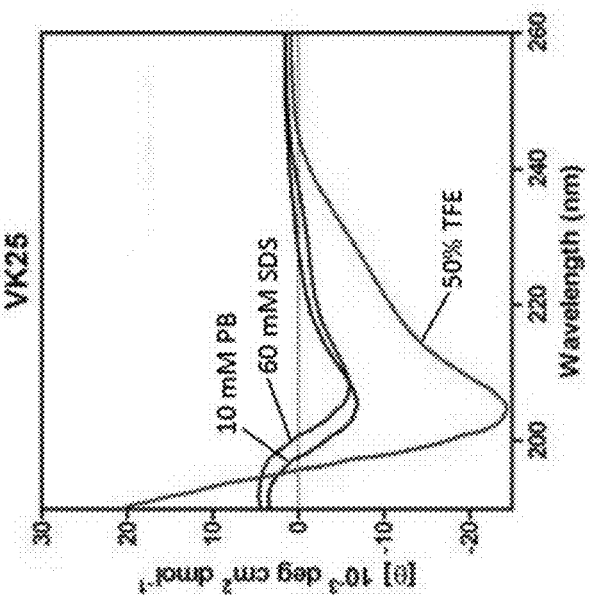
FIG. 6A
FIG. 6B
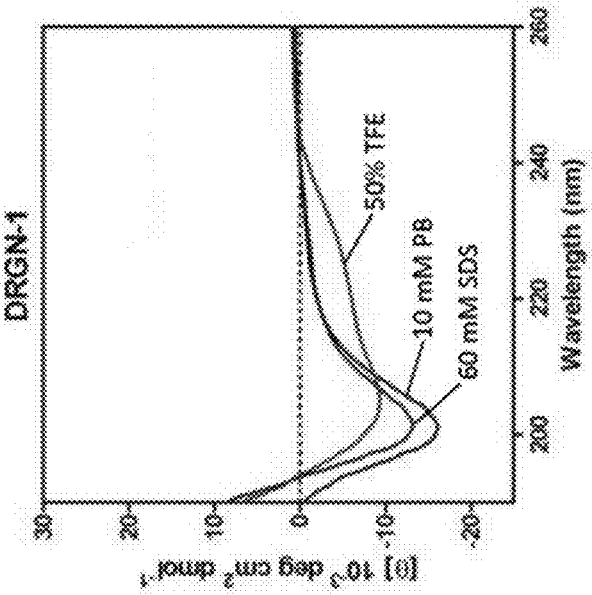
FIG. 6D
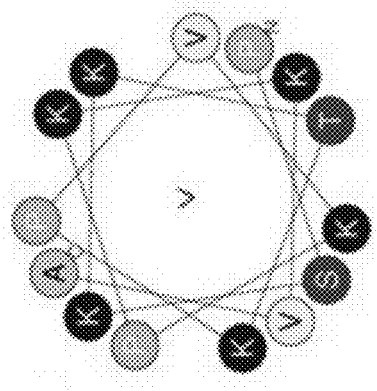
FIG. 6C

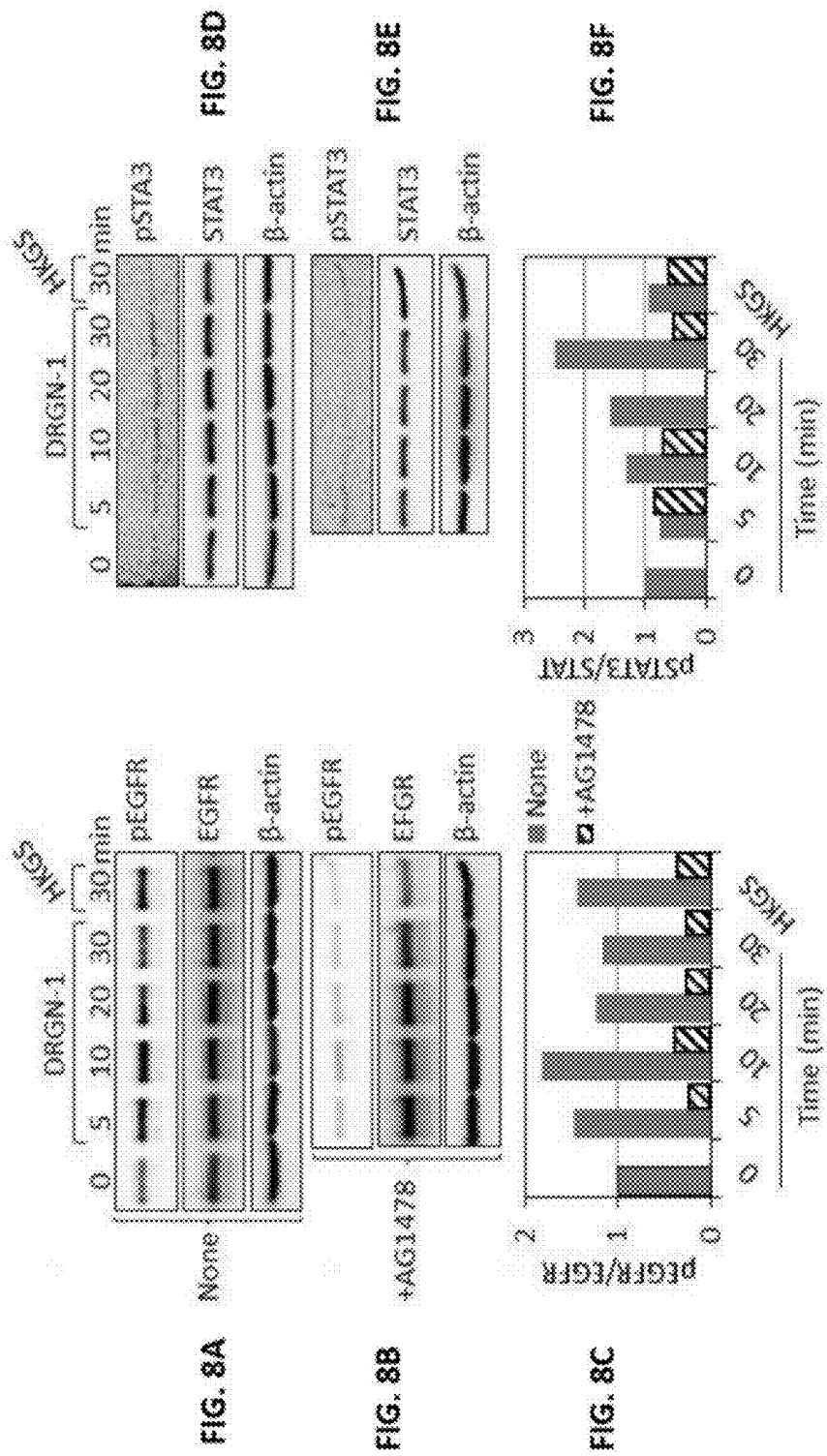

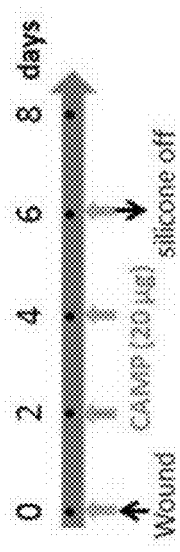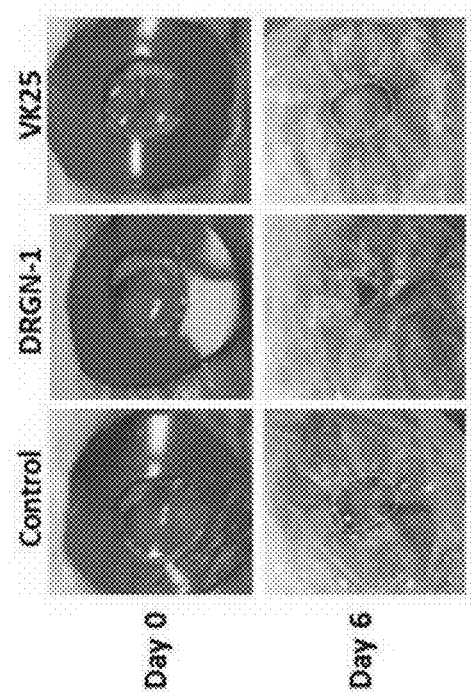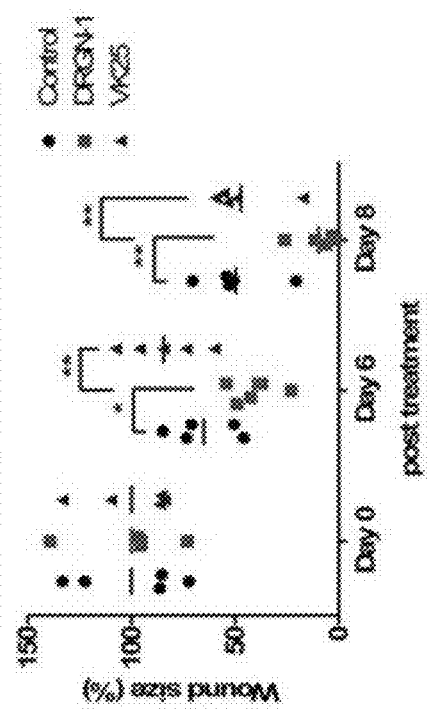
FIG. 9A
FIG. 9B
FIG. 9C

SEQUENCE LISTING

<160> NUMBER OF SEQ ID NOS: 11

<210> SEQ ID NO 1
<211> LENGTH: 14
<212> TYPE: PRT
<213> ORGANISM: Varanus komodoensis

<400> SEQUENCE: 1

Ser Pro Lys Lys Thr Lys Pro Val Lys Pro Lys Lys Val Ala
1               5                   10

<210> SEQ ID NO 2
<211> LENGTH: 14
<212> TYPE: PRT
<213> ORGANISM: Artificial Sequence -continued

```
<220> FEATURE:
<223> OTHER INFORMATION: synthetic peptide

<400> SEQUENCE: 2

Pro Ser Lys Lys Thr Lys Pro Val Lys Pro Lys Lys Val Ala
1               5                   10

<210> SEQ ID NO 3
<211> LENGTH: 37
<212> TYPE: PRT
<213> ORGANISM: Homo sapiens

<400> SEQUENCE: 3

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

Lys Arg Ala Lys Lys Phe Phe Lys Lys Leu Lys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: C-terminal amide

<400> SEQUENCE: 5

Ser Pro Lys Lys Thr Lys Pro Val Lys Pro Lys Lys Val Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: C-terminal amide

<400> SEQUENCE: 6

Pro Ser Lys Lys Thr Lys Pro Val Lys Pro Lys Lys Val Ala
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic peptide
```

```
<400> SEQUENCE: 7

Pro Ser Arg Arg Thr Arg Pro Val Arg Pro Arg Arg Val Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthetic peptide

<400> SEQUENCE: 8

Pro Ser Arg Arg Thr Arg Pro Trp Arg Pro Arg Arg Val Ala
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (14)..(14)
<223> OTHER INFORMATION: Xaa = Aib

<400> SEQUENCE: 9

Pro Ser Lys Lys Thr Lys Pro Val Lys Pro Lys Lys Val Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<223> OTHER INFORMATION: Xaa = D-Pro
<220> FEATURE:
<221> NAME/KEY: MISC_FEATURE
<222> LOCATION: (1)..(1)
<223> OTHER INFORMATION: Xaa = D-Pro

<400> SEQUENCE: 10

Xaa Ser Lys Lys Thr Lys Pro Val Lys Pro Lys Lys Val Ala
1               5                   10

<210> SEQ ID NO 11
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa = D-Ser

<400> SEQUENCE: 11

Pro Xaa Lys Lys Thr Lys Pro Val Lys Pro Lys Lys Val Ala
1               5                   10
```

ANTIMICROBIAL PEPTIDES WITH WOUND HEALING ACTIVITY

CROSS-REFERENCE TO RELATED APPLICATIONS

This application is a National Stage Entry of International Application No. PCT/US2017/044161, filed on Jul. 27, 2017, which claims benefit of priority to U.S. Provisional Application Ser. No. 62/367,238, filed on Jul. 27, 2016; and which said applications are incorporated herein by reference in their entireties.

GOVERNMENT INTERESTS

This invention was made with government support under grant number HDTRA1-12-C-0039 awarded by the Defenese Threat Reduction Agency. The government has certain rights in the invention.

REFERENCE TO SEQUENCE LISTING

The Sequence Listing concurrently submitted herewith as a text file named "G100_0003USPCT_Sequence_Listing.txt," created on Dec. 19, 2018, and having a size of 3,440 bytes is herein incorporated by reference pursuant to 37 C.F.R. § 1.52(e)(5).

FIELD OF THE INVENTION

This document relates to peptides with antimicrobial properties, to compositions containing such peptides, and to methods for using the peptides.

BACKGROUND

The rising tide of multidrug-resistant (MDR) pathogens ensures that the need for new antibiotics will continue to grow. This has led to antimicrobial peptides (AMPs) being considered as an alternative to conventional antibiotics, due to their potent and broad antimicrobial activity. The mode of AMP action is not fully understood, but their major targets are believed to be the cytoplasmic membrane and intracellular molecules (Pieters et al., *Protein Pept Lett* 16:736-742, 2009; and Nicolas, *FEBS J* 276:6483-6496, 2009). It is thought to be difficult for bacteria to develop resistance to antimicrobial peptides, because most AMPs kill bacterial cells quickly (Chan et al., *Biochim Biophys Acta* 1758:1184-202, 2006). Although small cationic peptides have a number of potential advantages as therapeutics, in vivo proteolysis and insufficient efficacy in animal model raise potential issues for clinical use.

SUMMARY OF THE INVENTION

Animals have developed evolving defenses to bacteria over millions of years. Reptiles, including the American alligator (*Alligator mississippiensis*) and other crocodilians, are evolutionarily ancient animals whose plasma and leukocyte extracts exhibit antimicrobial activity (Darville et al., *Comp Biochem Physiol Part D. Genomics Proteomics* 5:308-316, 2010; Cassir et al., *Front Microbiol* 5:551, 2014; and Fernández et al., *Antimicrob Agents Chemother* 56:1128-1132, 2012). This document is based at least in part on the discovery of novel AMPs from plasma obtained from the Komodo dragon (*Varanus komodoensis*), a large species of lizard found in the Indonesian island of Komodo. The saliva of the Komodo dragon is home to different strains of bacteria, some known to cause sepsis (Goldstein et al., *J Zoo Wildl Med* 44:262-272, 2013; and Montgomery et al., *J Wildl Dis* 38:545-551, 2002). This bacteria-laden saliva never sickens the Komodo dragon, however, suggesting that proteins in the dragon's blood provide immunity against the dangerous germs. As described herein, an AMP discovery platform (Bishop et al., *PLoS One* 10:e0117394, 2015) was used in the discovery of multiple Komodo dragon peptides with interesting antimicrobial properties, including a histone H1-derived peptide referred to herein as "VK25," as well as a short synthetic (non-natural) peptide containing a synthetic rearrangement of the amino acids at the N-terminal end of VK25. The synthetic peptide is referred to herein as "DRGN-1."

This document also is based at least in part on the discovery that DRGN-1 exhibits promising antimicrobial and antibiofilm properties. For example, DRGN-1 promotes wound healing in vitro and in vivo, in both uninfected and mixed biofilm infected wounds (e.g., in a murine model infected with the hospital acquired pathogens *Pseudomonas aeruginosa* and *Staphylococcus aureus*). In addition, DRGN-1 in combination with another antimicrobial peptide, ATRA1A, may have additional activities against bacteria and biofilms. Thus, DRGN-1 may be a potent wound healing agent in polymicrobial infected wounds. Further, since DRGN-1 does not affect the viability of human keratinocytes and erythrocytes, this peptide may be useful as a topical agent for infected wound treatment. For example, DRGN-1 may be a strong candidate in use as an alternative to antibiotics, and may be especially useful as a new treatment approach for chronically infected diabetic patients who often have chronic, non-healing wounds, as well as for soldiers who may have suffered combat wounds or burns.

In one aspect, this document features a purified peptide having a length of about ten to about twenty amino acids, wherein the peptide includes (a) the amino acid sequence set forth in SEQ ID NO:2, or (b) the amino acid sequence set forth in SEQ ID NO:2 with one substitution, addition, or deletion. The peptide can include one or more D-amino acid residues. In some embodiments, at least 50 percent of the amino acids in the peptide can be D-amino acids. The peptide can consist of D-amino acids.

In another aspect, this document features a composition containing one or more peptides as provided herein, and an excipient. The composition can contain about 0.01 µg/ml to about 10 µg/ml peptide, or about 0.05 µg/ml to about 25 µg/ml peptide. The composition can include a molecular crowding agent (e.g., a neutral, highly branched, high-mass, hydrophilic polysaccharide). The composition can further include a second purified peptide having a length of about ten to about twenty amino acids, where the peptide includes (a) the amino acid sequence set forth in SEQ ID NO:4, or (b) the amino acid sequence set forth in SEQ ID NO:4 with one substitution, addition, or deletion. The composition can be formulated for topical use.

In another aspect, this document features a method for treating an infection by a microbial organism, where the method includes contacting the microbial organism with a peptide or composition as provided herein. The microbial organism can be a bacteria or a fungus. The infection can be in or on a human patient. The composition can contain about 0.01 µg/ml to about 10 µg/ml peptide, or about 0.05 µg/ml to about 25 µg/ml peptide. After the contacting step, growth of the microbial organism can be reduced by at least about 5 percent when measured in an assay to measure colony formation. After the contacting, growth of the microbial organism can be reduced by at least about 50 percent when measured in an assay to measure colony formation. The composition can further include a second purified peptide having a length of about ten to about twenty amino acids, the peptide containing the amino acid sequence set forth in SEQ ID NO:4 or the amino acid sequence set forth in SEQ ID NO:4 with one substitution, addition, or deletion. The infection can be in a wound of a subject. The wound can be the result of an accident or the result of medical intervention. The infection can be a polymicrobial infection. The subject can be a diabetes patient, a member of the armed services, a fire fighter, or a worker in a gas, oil, or chemical industry.

This document also features a method for inhibiting the growth of a biofilm on a surface, where the method includes contacting the surface with a peptide or composition as provided herein. The surface can be an environmental surface. The surface can be on a prosthetic or an implant. The surface can be in a living organism (e.g., a human). After the contacting, growth of the biofilm can be reduced by at least about 5 percent, compared to a control, when measured in an assay to measure optical density. After the contacting, growth of the biofilm is reduced by at least about 25 percent, compared to a control when measured in an assay to measure optical density. The composition can further include a second purified peptide having a length of about ten to about twenty amino acids, the peptide comprising the amino acid sequence set forth in SEQ ID NO:4 or the amino acid sequence set forth in SEQ ID NO:4 with one substitution, addition, or deletion.

In still another aspect, this document features an article of manufacture containing a purified peptide as provided herein. The article can be a personal hygiene product. The article can be a wound dressing.

In another aspect, this document features a method for treating an infection in a subject in need thereof, where the method includes determining that the subject is resistant to one or more conventional antibiotics, or is suspected of being resistant to one or more conventional antibiotics; and treating the subject with a peptide or composition as provided herein.

In another aspect, this document features a method for improving the effectiveness of treatment for a microbial infection in a subject in need thereof, where the method includes (a) administering to the subject (i) an amount of a peptide as provided herein that is sub-anti-microbial but is effective to reduce biofilm levels or inhibit biofilm formation, or (ii) administering a peptide as provided herein under conditions that are sub-anti-microbial but are effective to reduce biofilm levels or inhibit biofilm formation; and (b) then administering to the subject (i) an anti-microbial amount of the peptide, or (ii) the peptide under conditions that are anti-microbial, or (iii) one or more conventional antibiotics. The peptide can be administered under high salt conditions (e.g., conditions that include 125 to 150 mM salt).

This document also features a method for promoting wound healing in a subject, wherein the method includes administering to the subject a peptide or composition as provided herein. The subject can be a vertebrate (e.g., a human). The composition can contain about 0.01 µg/ml to about 10 µg/ml peptide, or about 0.05 µg/ml to about 25 µg/ml peptide. The composition can further contain a second purified peptide having a length of about ten to about twenty amino acids, where the peptide contains the amino acid sequence set forth in SEQ ID NO:4 or the amino acid sequence set forth in SEQ ID NO:4 with one substitution, addition, or deletion. The wound may not be infected. The wound can be the result of an accident or medical intervention. The subject can be a diabetes patient, a member of the armed services, a fire fighter, or a worker in a gas, oil, or chemical industry.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2A is a graph plotting DRGN-1 antibiofilm activity against $S.$ $aureus$, analyzed using three interdependent methods. The activity was analyzed by crystal violet staining of biofilm in culture tube at 24 hours. FIG. 2B is a graph plotting DRGN-1 antibiofilm activity against $P.$ $aeruginosa$. The pictures (right inset in FIGS. 2A and 2B) are representative biofilms stained with crystal violet. P values were calculated using a two-tailed t test (assuming unequal variances) comparing test strains to untreated control ($*P<0.05$; $P<0.01$; $*P<0.001$). FIG. 2C is a series of confocal microscopy images taken for biofilm evaluation. Representative images of biofilms of $P.$ $aeruginosa$ PAO1-pTDK-GFP, $S.$ $aureus$ SH1000 pAH9-RFP, and mixed cultures exposed to PBS (control) or DRGN-1 (25 µg/ml) for 24 hours are shown. DRGN-1-exposed biofilms (bottom panels) were thinner and sparser than untreated controls (top panels). Scale bar: 20 µm.

FIGS. 3A-3F include light microscopy images of HEKa keratinocytes, and graphs plotting the effects of DRGN-1, VK25, and LL-37 at different concentrations on the number of metabolically active HEKa cells. FIGS. 3A-3D are light microscopy images. FIG. 3A shows uninfected control. About 100,000 cells were infected with $P.$ $aeruginosa$ ATCC 9027 ($1 \times 10^7$ CFU/ml) for 2 hours, washed with PBS, treated with gentamicin to remove extracellular bacteria for 1 hour, and incubated without peptide (FIG. 3B), with DRGN-1 (30 µg/ml) (FIG. 3C), or with VK25 (30 µg/ml) (FIG. 3D) for 2 hours at 37° C. FIG. 3E is a graph plotting bacterial survival within infected HEKa keratinocytes upon peptide treatment at 2 hours post treatment. FIG. 3F is a graph plotting the number of metabolically active cells, as determined by MTT assay and expressed as percentage with respect to non-peptide-treated control cells. P values were calculated using a two-tailed t test (assuming unequal variances) comparing test strains to untreated control ($*P<0.05$; $**P<0.01$).

FIGS. 5A-5C are graphs and images showing membrane permeability, membrane potential, and DNA binding of peptides. FIG. 5A is a graph plotting fluorescent dye uptake for EtBr by the P. aeruginosa ATCC 9027 in the presence of peptides (20 µg/ml). P values were calculated using a two-tailed t test (assuming unequal variances) comparing with untreated control at 20 min (**P<0.01). FIG. 5B is a graph plotting membrane depolarization as monitored by the change in the intensity of fluorescence emission of the membrane-potential-sensitive dye $DiSC_3(5)$ (excitation wavelength at 622 nm, emission wavelength at 670 nm) on addition of 20 µg/ml peptides or 0.1% Triton X-100 for a positive control. FIG. 5C is a picture of a gel showing the effect of peptides on the migration of DNA. Various amounts of peptides were incubated with 100 ng of plasmid DNA at room temperature for 15 minutes, and the reaction mixtures were applied to a 1% agarose gel electrophoresis. The fraction of unshifted DNA was calculated by densitometry (plotted in the bottom panel).

FIGS. 6A-6D relate to CD spectra of peptides in the presence of SDS or TFE. FIGS. 6A and 6B show CD spectra of 100 µg/ml concentration of peptides in the presence of the indicated concentrations of sodium phosphate (PB), SDS, or TFE. FIG. 6C is a helical wheel plot of DRGN-1, as predicted by HeliQuest. FIG. 6D is a table showing the composition of α-helix conformation calculated from the ellipticity value at 222 nm using the relation (% α-helix= $([\theta_{222}]-3000)/(-36000-3000)$). The ratio $[\theta]_{222}/[\theta]_{208}$ obtained by circular dichroism (CD) spectroscopy is defined as the R2 value. R2>1 is the hallmark of coiled-coil α-helical structure with >80% helical content (Graddis et al., Biochemistry 32:12664-12671, 1993).

FIG. 7A is a picture showing confluent cells in medium with HGKS after wounding by a scratch with a pipette tip, and "gap" closure in the presence of peptides (10 µg/ml) as monitored by light microscopy at 0, 7, and 24 hours post peptide treatment. FIG. 7B is a graph plotting relative wound closure, calculated from micrographs using ImageJ software. The results shown were combined from three independent experiments; error bars represent the mean±SD. FIG. 7C is a picture showing HEKa cells that were preincubated with 20 µM mitomycin C for 90 minutes or 0.2 µM AG1478 for 10 minutes and subsequently treated or not with 10 µg/ml DRGN-1, as indicated. In parallel, cells treated with the peptide alone were included for comparison. Cells incubated with medium served as a control (Ctrl). FIG. 7D is a graph plotting relative wound closure. All data are the means of at least three independent experiments±SE. The levels of statistical significance between groups are indicated as follows: *P<0.05.

FIGS. 8A-8F indicate transactivation of the EGFR-STAT pathway by DRGN-1. Subconfluent keratinocytes were starved for 2 hours in HGKS-free medium and then stimulated with 10 µg/ml DRGN-1. For EGFR inhibition, cells were preincubated with 0.2 µM AG1478 for 10 minutes and subsequently treated with 10 µg/ml DRGN-1. The cells were harvested into lysis buffer at the indicated times. The phosphorylation of EGFR (p-EGFR) and STAT3 (p-STAT3) was analyzed by Western blotting (FIGS. 8A, 8B, 8D, and 8E). EGFR indicates total EGFR protein. FIGS. 8C and 8F are graphs plotting densitometric analyses of the expression of phosphoprotein relative to unphosphorylated proteins (pEGFR/EGFR, FIG. 8C; pSTAT3/STAT3, FIG. 8F).

FIGS. 9A-9C show the wound healing activity of DRGN-1 in a mouse full-thickness skin wound model. FIG. 9A is a schematic of the experimental design, including the timing of drug treatments. FIG. 9B is a series of pictures showing the effect of DRGN-1 on closure of full-thickness excisional wounds (6-mm-diameter) in mice. Each wound was treated with DRGN-1 or VK25 every 48 hours (n=5 mice per group). The same animal was lightly anesthetized and photographed on the indicated days following injury. FIG. 9C is a graph plotting the changes in percentage of wound area at each time point in comparison to the original wound area. *P<0.05 and **P<0.01.

FIG. 10A is a schematic of the experimental design, including the timing of infection, drug treatments, and dressing off. FIG. 10B is a series of pictures indicating the effect of the indicated peptides on closure of P. aeruginosa/ S. aureus-infected wounds in mice. A 6-mm-diameter excision was made on the back of each mouse. The wounds were infected with a mixed biofilm (P. aeruginosa/S. aureus) grown on a polycarbonate membrane for 2 days. DRGN-1, VK25 or LL-37 (20 µg) was topically applied every 2 days in 1% hypromellose (n=5 mice per group). The same animal was lightly anesthetized with isoflurane and photographed on the indicated days following treatment. FIGS. 10C and 10D are graphs plotting bacterial colonization in S. aureus or P. aeruginosa-infected wounds, respectively. Wound tissue samples were harvested on day 6 after treatment, and the number of CFU/wound was counted in a selective medium for each species. The median value in each group is shown as a horizontal bar (n=5; p<0.01 and *P<0.001).

DETAILED DESCRIPTION OF THE INVENTION

Figures 1A, 1B:
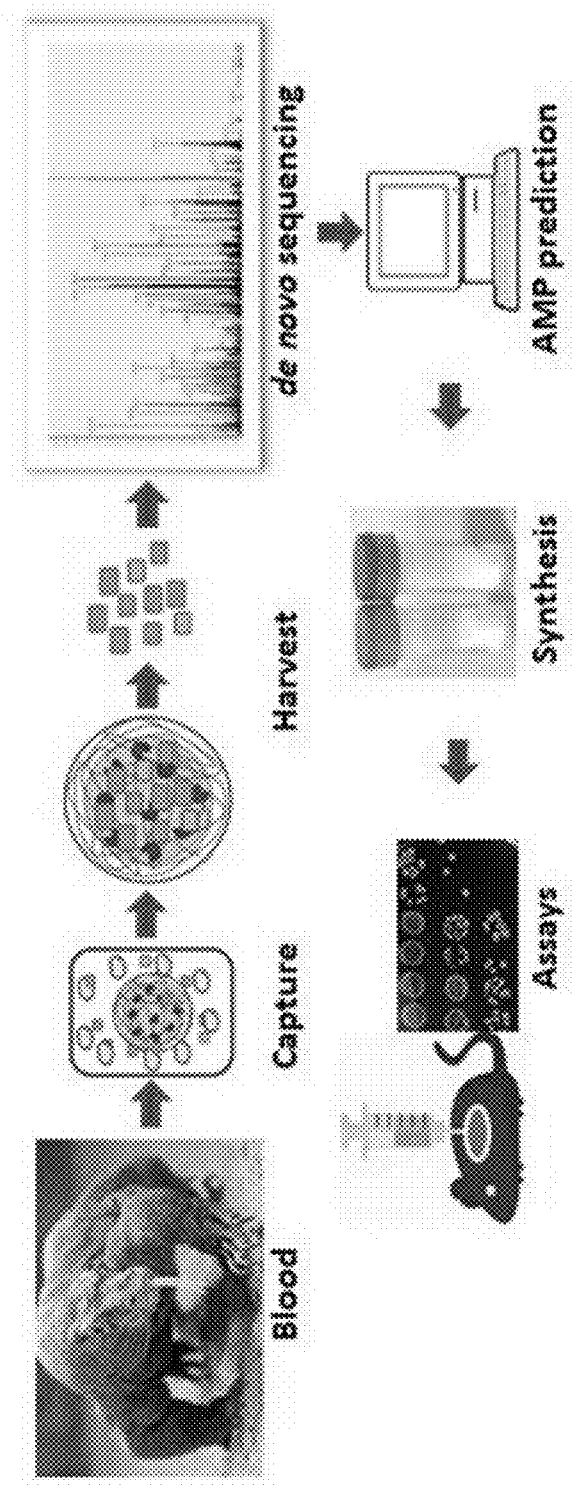
FIG. 1A is a schematic outlining experimental procedures used to identify an antimicrobial peptide from Komodo dragon.
FIG. 1B shows the amino acid sequence of the VK25 peptide (SEQ ID NO:1) as determined "de novo" by analyzing the peak differences in the fragmentation spectrum.

This document provides materials and methods related to AMPs, and strategies for leveraging the therapeutic potential of AMPs. AMPs as described herein, and compositions containing the AMPs, can be used to treat or inhibit microbial infections, and to prevent or reduce biofilm formation, for example.

Biofilms are aggregates of microorganisms in which cells adhere to each other on a surface. The adherent cells frequently are embedded in a self-produced matrix of extracellular polymeric substance (EPS) that generally is composed of extracellular DNA, proteins, and polysaccharides. Biofilms are ubiquitous, and can form on virtually any non-shedding, living or non-living surface in a non-sterile aqueous (or very humid) environment. Biofilms can be found, for example, in natural, industrial and hospital settings (Hall-Stoodley et al., Nat Rev Microbiol 2(2):95-108, 2004; and Lear and Lewis (eds.) (2012) *Microbial Biofilms: Current Research and Applications*, Caister Academic Press). Biofilms can be involved in a wide variety of microbial infections in the body ("Research on microbial biofilms (PA-03-047)," NIH, National Heart, Lung, and Blood Institute, 2002), including common problems such as urinary tract infections, catheter infections, ear infections, formation of dental plaque, gingivitis, coating contact lenses, and less common but more serious conditions such as endocarditis, infections in cystic fibrosis, and infections of permanent indwelling devices such as joint prostheses and heart valves (Rogers (2008) *Molecular Oral Microbiology*, Caister Academic Press, pp. 65-108; Imamura et al. (2008) *Antimicrob. Agents Chemother.* 52(1):171-182; Lewis (2001) *Antimicrob. Agents Chemother.* 45(4):999-1007; and Parsek and Singh (2003) *Ann. Rev. Microbiol.* 57:677-701). Bacterial biofilms also can impair cutaneous wound healing and reduce topical antibacterial efficiency in healing or treating infected skin wounds (Davis et al., *Wound Repair Regen* 16(1):23-29, 2008).

Chronic opportunistic infections in immunocompromised patients and the aging population are a major challenge for medical professionals, as traditional antibiotic therapies usually are not sufficient to eradicate the infections. One reason for their persistence seems to be the capability of the bacteria to grow within biofilms that protect them from adverse environmental factors. *Pseudomonas aeruginosa* is an example of an opportunistic pathogen and a causative agent of emerging nosocomial infections. Other examples of microbes that can form medically relevant biofilms include, without limitation, *Streptococcus mutans* and *Streptococcus sanguinis*, which are involved in formation of dental plaque (Rogers, supra), *Legionella* bacteria (Murga et al., *Microbiol* 147(Pt 11):3121-3126, 2001), and *Neisseria gonorrhoeae*, which can form biofilms on human cervical epithelial cells (Apicella et al. (2010) "Gonococcal Biofilms," in *Neisseria: Molecular Mechanisms of Pathogenesis*, Caister Academic Press, pp. 55-60).

The peptides and compositions described herein can be used for treatment of microbial (e.g., bacterial) infections and biofilms, including infections and biofilms that involve microbial strains that are resistant to antibiotics. These peptides and compositions can have enhanced potency against pathogenic organisms, and can be used, without limitation, for treating infections, as sensors, in sterilization procedures, in surface coatings, in wound dressings, and in personal hygiene products such as mouthwash and body wash.

Cationic antimicrobial peptides (CAMPs) are a defense mechanism pervasively employed by higher organisms to guard against infection. CAMPs can be loosely classified into four groups based on common structural themes: linear α-helical peptides, linear extended peptides with sequences dominated by one or more amino acids, peptides containing loop structures, and peptides with more defined structures constrained by intramolecular disulfide bonds (van't Hof et al., *Biol Chem* 382(4):597-619, 2001). It is notable that despite their extensive use for millions of years, bacteria have failed to develop widespread resistance to CAMPs. This is in stark contrast to the rampant spread of bacterial resistance to conventional antibiotics that threatens the ability to effectively treat infections.

While CAMPs exhibit a diverse range of amino acid sequences and structural properties, they typically are small amphipathic peptides that are rich in lysine and arginine residues, and they exert a direct anti-microbial effect on a broad spectrum of microbes including Gram-positive and Gram-negative bacteria, and fungi. Although there is debate regarding the specific mechanisms employed by anti-microbial peptides and whether secondary targets are involved, CAMPs have been shown to attack bacterial membranes, ultimately disrupting their integrity (Brogden, *Nat Rev Microbiol* 3(3):238-250, 2005). The cationic peptides are thought to initially associate with the outer surface of bacterial membranes, which tend to contain a greater abundance of lipids with negatively charged head groups than do eukaryotic membranes. The presence of cholesterol in eukaryotic membranes also may contribute to their resistance to disruption by CAMPs. Multiple mechanisms for membrane disruption have been proposed, and these mechanisms appear to be peptide dependent. Proposed mechanisms range from a "barrel-stave" model in which where amphipathic helical peptides insert into the membrane to form helical bundle structures with large central pores, to a "carpet model" in which peptides gather and concentrate at the membrane surface to interact with anionic lipid head groups, causing distortions in the lipid bi-layer and formation of peptide-lined openings in the membrane. Due to the fundamental mechanism of action of CAMPs against bacterial membranes, bacteria are less likely to develop resistance to CAMPs than to traditional antibiotics.

Helical CAMPs are one of the most abundant classes of anti-microbial peptides (Tossi et al., *Biopolymers* 55(1):4-30, 2000). They are short (typically less than 40 amino acids), which facilitates their synthesis, and they have a simple, linear, amphipathic α-helix structure, which makes them amenable to characterization by spectroscopic methods such as circular dichroism (CD). In the absence of the influence of negatively charged bacterial membranes, helical CAMPs assume a relatively unstructured random coil, and only adopt a helical conformation when they interact and bind bacterial membranes. Formation of an amphipathic helix by a peptide can facilitate its insertion and integration into microbial membranes, and usually is essential to the anti-microbial mechanism employed by helical CAMPs. Unfortunately, because helical CAMPs are small peptides that have little or no structure until they interact with bacterial membranes, they are susceptible to degradation by proteases, which could reduce their potential therapeutic utility. Assembling the peptides out of D-amino acids, which are not recognized by proteases, can enable CAMPs to evade digestion and remain intact until reaching the membrane (Wade et al., *Proc Natl Acad Sci USA* 87(12):4761-4765, 1990). Peptides formed from all L- or all D-amino acids form helical structures that differ only by their handedness, with L-CAMPs adopting a right-handed helical conformation and D-CAMPs forming a left-handed helix.

Early studies of the D-enantiomers of three naturally occurring anti-microbial peptides (cecropin A, magainin 2 amide and melittin) and two designed peptides (chimeric peptides combining portions of cecropin A and melittin) did not indicate any significant differences in the anti-microbial or hemolytic properties of the D- and L-isomers (Wade et al., supra). This led to the suggestion that the peptides exert their anti-microbial effect without significant involvement of chiral elements within the bacterial membranes. Later studies, however, found significant differences in the anti-microbial performance of the D- and L-isomers of the cecropin A/melittin chimeric peptides (Vunnam et al., *J Pept Res* 51(1): 38-44, 1998), and attributed the superior anti-microbial potency of the D-isomers against *S. aureus* and *P. aeruginosa* at least in part to their resistance to degradation by microbial proteases. D- and L-enantiomers of pleurocidin, a helical CAMP from the winter flounder, also exhibited significant differences in their anti-microbial effectiveness against a panel of Gram-negative and Gram-positive bacteria (Lee and Lee, *Exp Mol Med* 40(4):370-376, 2008). The D-isomer also displayed much lower hemolytic activity than the corresponding L-peptide.

The properties that make anti-microbial peptides an effective defensive mechanism in higher organisms also can make them ideally suited as a platform for targeting microbes for delivery of anti-microbial compounds. This platform could provide a therapeutic tool for treating infections (e.g., infections of the gastrointestinal tract, respiratory system, circulatory system, lymphatic system, urinary system, muscular system, skeletal system, nervous system, or reproductive system), and could allow for the use of novel anti-microbial agents that otherwise would be unsuitable as therapeutics.

Some interior surfaces of the body, such as the respiratory and the gastrointestinal (GI) tracts, are topographically equivalent to exterior surfaces of the body. Because these surfaces are constantly exposed to potentially pathogenic microbes and are conducive to bacterial growth, novel therapeutic agents and strategies are needed for treating infections of the respiratory and GI tracts, particularly those caused by antibiotic resistant pathogenic microbes. Some agents, such as *Francisella tularensis, Bacillus anthracis*, and *Yersinia pestis*, are known to cause life-threatening pneumonic infections and may be rendered antibiotic resistant, and are of particular concern as potential biological weapons. Similarly, foodborne and waterborne pathogens such as *Shigella dysenteriae, Vibrio cholera*, and *Salmonella typhi* are considered potential biological threats that could be employed to contaminate food and/or water supplies. While infections by many of these microbes usually are responsive to treatment with antibiotics, illness resulting from intentional exposure would likely involve organisms that have been engineered to be resistant to conventional antibiotics.

As described herein, newly discovered CAMPs may provide a solution to such problems. Technology described elsewhere was used to capture and identify antimicrobial peptides present in reptilian blood (Bishop et al., supra). As set forth in FIG. 1, small peptides were harvested from Komodo dragon blood using a nanoparticle-capturing technique. The peptides were subjected to mass spectral analysis using an Orbitrap Elite mass spectrometer equipped with electron transfer dissociation (ETD) to determine their sequences in a de novo manner. The sequences were compared to available genomic and proteomic information in order to confirm, complete, and correct the de novo peptide sequences. All sequences were ultimately manually verified, especially those for which no genomic information was available. Two selection criteria were applied to down-select peptides for further testing. In one approach, potential AMPs were identified from the peptide sequences using web-based prediction tools (AMP database, AntiBP2 and APD2). In the other approach, prospective AMPs were selected through rational analysis of the peptide sequences, focusing primarily on size, charge, and sequence similarity with other potential AMPs. For further testing, identified AMPs were synthesized to determine their antimicrobial activities. One Komodo dragon peptide, referred to herein as VK25, appeared promising based on its cationic sequence (SPKKTKPVKPKKVA; SEQ ID NO:1), small size (14 amino acids), and high positive charge (+6). This peptide was found to have some antimicrobial and/or anti-biofilm activity.

A synthetic peptide inspired by VK25 was then prepared by switching the first two amino acids. This peptide is referred to as DRGN-1, and has the sequence PSKKTKPVKPKKVA (SEQ ID NO:2). As described in the Examples below, DRGN-1 had strong antimicrobial, antibiofilm, and in vivo wound healing activity in a murine model infected with the hospital-acquired pathogens, *P. aeruginosa* and *S. aureus*. The activity of DRGN-1 against *P. aeruginosa* and *S. aureus* in terms of antibacterial and anti-biofilm activity in vitro or within infected HEKa keratinocytes also was assessed, as was its mode of action, and its ability to promote closure of a wound field produced in a keratinocyte monolayer. In addition, DRGN-1 was evaluated for wound healing activity in a murine model with polymicrobial biofilm-infected wounds. DRGN-1 performed significantly better than the human cathelicidin peptide LL-37 in vivo against an infected wound; LL-37 is a good comparator due to published reports of LL-37 having this activity.

Thus, this document provides AMPs based on the DRGN-1 amino acid sequence, as well as compositions containing one or more DRGN-1 based AMPs, and methods for using the peptides and compositions as antibacterial, antibiofilm, and wound healing agents. In some embodiments, for example, the peptides and compositions provided herein can be used as topical applications for diabetic patients who often have chronic, non-healing wounds, and for soldiers who may have suffered combat wounds or burns. In some embodiments, compositions containing one or more DRGN-1 based AMPs in combination with one or more other AMPs may have enhanced activity against bacteria or biofilms. Examples of other AMPs that may be useful include, without limitation, peptides containing the sequence KRAKKFFKKLK-NH$_2$ (SEQ ID NO:4, referred to herein as ATRA1A).

The peptides provided herein can have a length between about 10 amino acids and about 50 amino acids. For example, a peptide can have a length of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, a peptide can have a length of, without limitation, about 10 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, about 45 to about 50 amino acids, about 10 to about 20 amino acids, about 20 to about 30 amino acids, about 30 to about 40 amino acids, or about 40 to about 50 amino acids. In some cases, smaller peptides can be more useful than larger and/or more complex CAMPs, because smaller peptides are more easily synthesized and characterized.

The sequence of an anti-microbial peptide can be based on the sequence of the 14-residue DRGN-1 peptide, which has the sequence PSKKTKPVKPKKVA (SEQ ID NO:2). The peptides provided herein can be shorter, longer, or variant versions of the DRGN-1 peptide.

For example, the peptides provided herein can include one or more (e.g., one, two, three, four, or five) substitutions, deletions, or additions as compared to the DRGN-1 sequence set forth in SEQ ID NO:2. In some embodiments, a peptide can have an amino acid sequence with one or more (e.g., one, two, or three) substitutions, additions, or deletions relative to the sequence set forth in SEQ ID NO:2. Amino acid substitutions can be conservative or non-conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Non-conservative amino acid substitutions typically entail exchanging a member of one of the classes described above for a member of another class. After making an amino acid substitution, the activity of a peptide containing the amino acid substitution can be assessed using the assays described herein.

Examples of modified DRGN-1 peptides include, without limitation, peptides in which one or more lysine residues are replaced with arginine [(e.g., DRGN-R; PSRRTRPVR-PRRVA (SEQ ID NO:7)], peptides in which one or more lysine residues are replaced with arginine and one or both valines are replaced with tryptophan [(e.g., DRGN-RW; PSRRTRPWRPRRVA (SEQ ID NO:8)], peptides in which the C-terminal alanine is replaced with α-aminoisobutyric acid (Aib), also referred to as 2-methylalanine [e.g., DRGN-1X; PSKKTKPVKPKKVX, where X=Aib (SEQ ID NO:9)], and peptides in which one or more amino acids are replaced by their D-isoform [e.g., DRGN-1p; pSKKTKPVKPKKVA, where p=D-Pro (SEQ ID NO:10) or DRGN-1s; PsKKTK-PVKPKKVA, where s=D-Ser (SEQ ID NO:11)].

In some cases, a peptide as provided herein can have a C-terminal amide. Thus, a peptide can have the sequence SPKKTKPVKPKKVA-NH$_2$ (SEQ ID NO:5), or PSKKTK-PVKPKKVA-NH$_2$ (SEQ ID NO:6).

In some embodiments, a peptide as provided herein can be a fragment of DRGN-1 or VK25 (SEQ ID NO:1 or SEQ ID NO:2, respectively) that retains one or more biological (e.g., antimicrobial) activities of DRGN-1 or VK25. A fragment can have a length of about 8 to 13 (e.g., 8-10 amino acids, 9-11 amino acids, 10-12 amino acids, 11-13 amino acids, or 12-13 amino acids, for example).

The term "amino acid" as used herein refers to natural amino acids, unnatural amino acids, and amino acid analogs, all in their various stereoisomers (e.g., D and L stereoisomers or other allostereomers if their structures so allow). Natural (or "naturally-occurring") amino acids include the 20 "standard" amino acids that are encoded by the codons of the universal genetic code (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), as well as other "non-standard" amino acids that occur naturally but are not encoded by the codons of the universal genetic code (e.g., hydroxyproline, selenomethionine, and norleucine). Amino acids that are non-standard and/or non-naturally occurring include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native peptides, but differs in composition such that either the C-terminal carboxy group, the N-terminal amino group, or the side-chain functional group has been chemically modified or replaced with another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring, or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, *The Peptides: Analysis, Synthesis, Biology*, Academic Press, Inc., New York (1983).

The stereochemistry of a peptide can be described in terms of the topochemical arrangement of the side chains of the amino acid residues about the peptide backbone, which is defined by the peptide bonds between the amino acid residues and the I-carbon atoms of the bonded residues. In addition, polypeptide backbones have distinct termini and thus direction. The majority of naturally occurring amino acids are L-amino acids (including the 20 standard amino acids as well as a number of other naturally-occurring, non-standard amino acids), and naturally occurring, ribosomally-produced polypeptides are largely comprised of L-amino acids. D-amino acids are the enantiomers of L-amino acids. The peptides provided herein can be made up of L-amino acids, D-amino acids, or a combination thereof. For example, a peptide can have an amino acid composition in which at least 10% (e.g., at least 10%, at least 20%, at least 25%, at least 30%, at least 40%, at least 50%, at least 60%, at least 70%, at least 75%, at least 80%, at least 85%, at least 90%, at least 95%) of the amino acids are D-amino acids. It is to be noted that some amino acid residues have more than one stereocenter, and the peptides provided herein can include diastereomers of these amino acids that differ from each other only in the configuration of one of their stereocenters.

In some embodiments, peptidomimetic compounds can be used in place of the peptides provided herein. As used herein, the term "peptidomimetic" refers to compounds that are synthetic, non-peptide compounds having a three-dimensional conformation (a "peptide motif") that is substantially the same as the three-dimensional conformation of a selected peptide; a peptidomimetic compound therefore can essentially reproduce elements of amino acid structural properties and can confer the same or similar function as the selected peptide. As compared to a selected polypeptide, a peptidomimetic compound includes non-naturally occurring modifications, such as an altered backbone and/or non-natural amino acids. In some cases, for example, peptidomimetics can include beta-amino acids, peptoids, and/or N-methyl amino acids.

Peptidomimetic compounds can include amide ("peptide") or non-amide ("non-peptide") bonds in their backbone structure, or can include a combination of peptide and non-peptide bonds in their backbone structure. Peptidomimetic compounds that are protease resistant or that have additional characteristics that enhance therapeutic utility, such as increased cell permeability and prolonged biological half-life, can be particularly useful. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, sulfonamide, reduced carbonyl, dimethylene and ketomethylene) can be useful substitutes for peptide bonds in the construction of peptidomimetic compounds. In some embodiments, the compounds provided herein include hybrids that contain one or more peptide portions and one or more peptidomimetic portions. Such hybrid peptides can incorporate a combination of natural amino acids and mimetic amino acids (e.g., standard amino acids and peptoids) in the same molecule.

The peptides provided herein can be obtained by any of a number of methods, including those known in the art. In some embodiments, a peptide can be obtained by extraction from a natural source (e.g., from isolated cells, tissues or bodily fluids), or can be produced by expression of a recombinant nucleic acid encoding the peptide, or by chemical synthesis (e.g., using solid phase peptide synthesis methods or a peptide synthesizer such as an ABI Peptide Synthesizer; Applied Biosystems; Foster City, Calif.). For example, standard recombinant technology using an expression vector encoding a peptide provided herein can be used. The resulting peptide then can be purified using, for example, affinity chromatographic techniques and HPLC. The extent of purification can be measured by any appropriate method, including but not limited to: column chromatography, polyacrylamide gel electrophoresis, or high-performance liquid chromatography. In some cases, a peptide can be designed or engineered to contain a tag sequence that allows the peptide to be purified (e.g., captured onto an affinity matrix). For example, a tag such as c-myc, hemagglutinin, polyhistidine, or FLAG™ tag (Kodak) can be used to aid peptide purification. Such tags can be inserted anywhere within the peptide, including at either the carboxyl or amino terminus. Other fusions that can be used include enzymes that aid in the detection of the peptide, such as alkaline phosphatase. In some embodiments, a peptide can be amidated at its carboxy terminus.

In some cases, a peptide provided herein can be purified. A "purified peptide" is a peptide that either has no naturally occurring counterpart (e.g., a peptidomimetic), or has been chemically synthesized and is thus uncontaminated by other peptides, or has been recombinantly produced and has been separated from components of the cell in which it was produced, or that has been separated or purified from other cellular components by which it is naturally accompanied (e.g., other cellular proteins, polynucleotides, or cellular components). Typically, a peptide is considered "purified" when it is at least 70%, by dry weight, free from the proteins and other molecules with which it naturally associates. A preparation of a purified peptide therefore can be, for example, at least 80%, at least 90%, or at least 99%, by dry weight, the peptide. Suitable methods for purifying peptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

The anti-microbial, anti-biofilm, and wound healing activities of the peptides provided herein can be tested using any of a number of suitable methods, including those described in the Examples herein. The activity of a peptide against bacteria such as $P.$ $aeruginosa$ or $S.$ $aureus$, for example, can be tested by culturing the bacteria in a suitable liquid medium until cells reach a desired density (e.g., $OD_{600}$ of 0.8 to 1.1), and then diluting the cells to a suitable concentration in buffer containing varying concentrations of one or more selected peptides. Peptide concentrations used in the assays can range from 0 µg/ml to about 100 µg/ml with intermediate concentrations (e.g., about 0.01 µg/ml, 0.05 µg/ml, 0.1 µg/ml, 0.5 µg/ml, 1 µg/ml, 2.5 µg/ml, 5 µg/ml, 7.5 µg/ml, 10 µg/ml, 25 µg/ml, 50 µg/ml, 75 µg/ml, about 0.01 µg/ml to about 0.1 µg/ml, about 0.05 µg/ml to about 0.5 µg/ml, about 0.1 to about 1 µg/ml, about 0.5 µg/ml to about 5 µg/ml, about 2.5 µg/ml to about 10 µg/ml, or any other range between about 0.01 µg/ml and about 100 µg/ml) that vary for each peptide in order to maximize the number of data points. Assay cultures can be incubated for a desired length of time (e.g., about two hours), and serial dilutions of each sample can be prepared and plated. After a suitable length of incubation, colonies can be counted to determine the effectiveness of the peptide(s).

Bacterial survival at each peptide concentration can be calculated according to the ratio of the number of colonies on the plates corresponding to the peptide concentration and the average number of colonies observed for assay cultures lacking peptide. The peptide concentration required to kill about 50% of the viable cells in the assay cultures ($EC_{50}$) can be determined by plotting percent survival as a function of the log of peptide concentration (log µg/ml) and fitting the data to Equation (1) using, for example, GraphPad Prism (GraphPad Software, Inc., San Diego, Calif.), which describes a sigmoidal dose-response.

$$S = S_B((S_T - S_B)/(1 + 10^{(Log\ EC50 - X)H})) \quad (1)$$

In Equation (1), S is percent survival, $S_T$ and $S_B$ represent the upper and lower survival boundaries, X is the log of the peptide concentration, and H is the Hill slope of the transition region. Another form for Equation (1) is:

$$Y = Bottom + ((Top - Bottom)/(1 + 10^{[(log\ EC50 - X)*Hill\ Slope)]})) \quad (1)$$

where Y corresponds to bacterial survival (in percentage) at a given peptide concentration (µg/ml), with X being the logarithm of that concentration. In the equation, "Top" and "Bottom" refer to the upper and lower boundaries and were constrained to values <100% and >0%, respectively.

The effect of a peptide on biofilm production can be assessed by, for example, incubating a biofilm-forming bacteria or other microbe with varying concentrations of one or more peptides for a certain length of time (e.g., 24 hours at 37° C.). Optical density of the cultures (e.g., at $OD_{600}$ nm) can be measured to assess microbial growth, and cultures then can be stained with crystal violet to assess biofilm production. See, e.g., Durham-Colleran et al., $Microb$ $Ecol$ 59(3):457-465, 2010.

Peptides as provided herein can be formulated as in compositions by admixture with one or more pharmaceutically acceptable, non-toxic excipients or carriers. Such compositions can be used to treat or prevent microbial infection, for example. In some embodiments, a composition can include one particular peptide, while in other embodiments a composition can include two or more different peptides (e.g., peptides having different sequences or different amounts of D- and L-amino acids). For example, in some embodiments, a composition can contain a DRGN-1 peptide having the amino acid sequence set forth in SEQ ID NO:2, with or without a second ATRA1A peptide having the amino acid sequence set forth in SEQ ID NO:4. The compositions provided herein can contain one or more peptides at a concentration of about 0.001 µg/ml to about 100 µg/ml (e.g., about 0.001 µg/ml to about 0.01 µg/ml, about 0.005 µg/ml to about 0.05 µg/ml, about 0.01 µg/ml to about 1 µg/ml, about 0.01 µg/ml to about 10 µg/ml, about 0.05 µg/ml to about 5 µg/ml, about 0.05 µg/ml to about 25 µg/ml, about 0.1 µg/ml to about 10 µg/ml, about 0.5 µg/ml to about 50 µg/ml, about 1 µg/ml to about 100 µg/ml, or about 10 µg/ml to about 100 µg/ml.

Excipients (also referred to as pharmaceutically acceptable carriers) can be liquid or solid, and can be selected with the planned manner of administration in mind so as to provide for the desired bulk, consistency, and other pertinent transport and chemical properties, when combined with one or more of peptides and any other components of a given composition. Common excipients include, without limitation, sterile water, saline, polyalkylene glycols such as polyethylene glycol, oils of vegetable origin, hydrogenated naphthalenes, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some cases, biocompatible, biodegradable lactide polymer, lactide/glycolide copolymer, polyoxethylene-polyoxypropylene copolymers, or combinations thereof can be used as excipients for controlling the release of a peptide in vivo.

In some embodiments, a composition can include a peptide and one or more molecular crowding agents such as, by way of example and not limitation, FICOLL™ (e.g., FICOLL™ 70), polyethylene glycol (PEG), and dextran. FICOLL™ is a neutral, highly branched, high-mass, hydrophilic polysaccharide that dissolves readily in aqueous solutions. PEG is a polymer of ethylene oxide, and is commercially available over a wide range of molecular weights from 300 g/mol to 10,000,000 g/mol. Dextran is a complex, branched polysaccharide made of glucose molecules. Without being bound by a particular mechanism, such agents may help to mimic the natural cellular environment, which may enhance the activity of the peptide. Such agents can be included in the compositions in amounts from about 5% to about 50% wt/vol (e.g., about 5%, about 10%, about 15%, about 20%, about 25%, about 30%, about 35%, about 40%, about 45%, or about 50% wt/vol, or any range there between, including 5% to 10%, 10% to 20%, 20% to 25%, 25% to 30%, 30% to 40%, or 40% to 50%).

In some embodiments, pharmaceutical compositions also can include one or more conventional antibiotics (e.g., amoxicillin, cephalexin, bacteriocin, neomycin, and/or polymyxin) and/or active ingredients from wound dressings or wound treatment compositions (e.g., NEOSPORIN®, bacitracin, and silver sulfadiazine).

Compositions can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations). Compositions for other routes of administration also can be prepared as desired using appropriate methods. In addition, compositions can be prepared for in vitro use (e.g., for use on environmental surfaces or on medical devices).

Formulations for topical administration of peptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions can include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations can be useful for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidyl-choline, dimyristoyl phosphatidylglycerol, or dioleoyl phosphatidylethanolamine. Numerous lipophilic agents are commercially available, including LIPOFECTIN® (Invitrogen/Life Technologies, Carlsbad, Calif.) and EFFECTENE™ (Qiagen, Valencia, Calif.).

The peptides provided herein further encompass pharmaceutically acceptable salts, esters, or salts of such esters, or any other compound which, upon administration to an animal including a human, is capable of providing (directly or indirectly) the biologically active metabolite or residue thereof. Accordingly, for example, provided herein are pharmaceutically acceptable salts of peptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the peptides described herein (i.e., salts that retain the desired biological activity of the parent peptide without imparting undesired toxicological effects). Examples of pharmaceutically acceptable salts include, without limitation, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., acetic acid, citric acid, oxalic acid, palmitic acid, or fumaric acid).

Compositions additionally can contain other adjunct components such as, for example, lubricants, preservatives, stabilizers, wetting agents, emulsifiers, salts for influencing osmotic pressure, buffers, colorings, flavorings, and aromatic substances. When added, however, such materials should not unduly interfere with the biological activities of the peptide components within the compositions provided herein. The formulations can be sterilized if desired.

Subjects that can be treated using the peptides and compositions provided herein include vertebrates such as, without limitation, mammals (e.g., humans, non-human primates, horses, dogs, cats, cows, rodents, sheep, pigs, and goats), birds, and fish.

Dosing of compositions for administration to a subject typically is dependent on the severity and responsiveness of the condition to be treated, with the course of treatment lasting from several days to several months, or until a cure is effected or a diminution of the condition is achieved. Persons of ordinary skill in the art routinely determine optimum dosages, dosing methodologies and repetition rates. Optimum dosages can vary depending on the relative potency of individual peptides, and can generally be estimated based on $EC_{50}$ found to be effective in in vitro and in vivo animal models. Typically, dosage is from 0.01 µg to 100 g per kg of body weight, and may be given once or more daily, biweekly, weekly, monthly, or even less often. Following successful treatment, it may be desirable to have the patient undergo maintenance therapy to prevent the recurrence of the disease state.

It is noted that treatments may differ if a patient is resistant or suspected of being resistant to certain antibiotics. For example, if a patient has an infection that is resistant to antibiotics, the dose may be increased or the treatment may include two or more different peptides.

The peptides and compositions described herein also can be used in the manufacture of medicaments for treating microbial infection or for inhibiting or reducing biofilm growth. One or more peptides can be admixed, encapsulated, conjugated or otherwise associated with other molecules, molecular structures, conventional antibiotics, or mixtures of compounds such as, for example, liposomes, polyethylene glycol, receptor targeted molecules, or oral, topical or other formulations, for assisting in uptake, distribution, absorption, or activity.

This document also provides methods for using the peptides and compositions described herein to inhibit microbial growth, to reduce or prevent biofilm formation. In some embodiments, for example, a composition containing an anti-microbial, helical peptide as described herein can be used to treat a subject having a microbial (e.g., bacterial or fungal) infection, such as in a wound that is in or on a subject (e.g., a mammal such as, without limitation, a human). Wounds can result from accidental occurrences, or can result from, for example, medical procedures. In some embodiments, the subject can be a human who is a medical patient (e.g., a diabetes patient, or a patient in a hospital or clinic setting), a member of the armed services or law enforcement, a fire fighter, or a worker in the gas, oil, or chemical industry.

In some embodiments, a composition containing an AMP can be used to inhibit or prevent biofilm growth, either in vivo by administration to a subject, or in vitro such as in a sterilization procedure for an environmental surface (e.g., in a hospital, a public restroom, or another public setting). The peptides and compositions described herein also can be used in surface coatings for medical devices (e.g., catheters, prosthetics, implants, and other indwelling devices), or in dressings to be applied to wounds on or in a patient. In some cases, the peptides provided herein can be formulated into compositions that serve as personal hygiene products, including mouthwash, hand sanitizer, or body wash. Further, in some embodiments, the methods provided herein can include the use of an AMP in combination with one or more conventional antibiotics (e.g., amoxicillin, cephalexin, bacteriocin, neomycin, and/or polymyxin).

The peptides and compositions also can be used in methods that include determining whether a subject having a microbial infection is resistant to one or more conventional antibiotics (e.g., methicillin), or is suspected of being resistant to one or more conventional antibiotics. If the subject is determined to be resistant to the one or more conventional antibiotics, or is suspected of being resistant to the one or more conventional antibiotics, s/he can be treated with a peptide or composition provided herein. In contrast, if the subject is determined not to be resistant to the one or more conventional antibiotics, or is not suspected of being resistant to the one or more conventional antibiotics, s/he can be treated with the one or more conventional antibiotics. In such methods, the subject can be monitored to determine whether the treatment is effective, and the treatment can be adjusted accordingly. For example, if the subject is treated with one or more conventional antibiotics but is subsequently determined to be resistant to the conventional antibiotic(s), the subject can be treated with a peptide or composition as provided herein. In some embodiments, the subject can be treated with one or more AMPs and conventional antibiotics contemporaneously (e.g., in cases of severe infection insufficient time to try one or the other treatments).

In addition, the peptides and compositions provided herein can be used in methods for improving the effectiveness of treatment for microbial infection. For example, a method can include administering to a subject an amount of a peptide or composition that is sub-anti-microbial but is effective to reduce biofilm levels or inhibit biofilm formation, or administering a peptide under conditions that are sub-anti-microbial but are effective to reduce biofilm levels or inhibit biofilm formation. For example, a peptide may be less effective as an anti-microbial agent under high salt conditions (e.g., about 125 to about 150 mM salt, including about 130 mM, about 135 mM, about 140 mM, or 145 mM salt), but can retain effectiveness as an anti-biofilm agent under such conditions. After one or more sub-anti-microbial treatments, the subject can be treated with an anti-microbial amount of the peptide or composition, with the peptide under conditions that are anti-microbial, or with one or more conventional antibiotics. The sub-anti-microbial and anti-microbial treatments can be separated by any length of time, ranging from an hour or less to several hours to a day or more (e.g., about 0.5 hour, about one hour, about two hours, about three hours, about four hours, about six hours, about 12 hours, about 1 day, or more than 1 day). Treatments can be repeated as needed or desired.

The effectiveness of a peptide or composition containing one or more peptides as described herein can be determined by assessing microbial growth or biofilm growth before, during, and/or after treatment. In some embodiments, for example, samples can be obtained from a subject before treatment, and at one or more different time points during or after treatment with a peptide or composition as provided herein, and microbial growth can be measured by counting the number of colonies that grow up from the samples after they are plated on a solid medium. Biofilm growth can be measured based on optical density (e.g., at 600 nm) and/or staining with crystal violet, for example. Treatment with a peptide or composition can be considered effective if microbial growth or biofilm formation is reduced by at least 5% (e.g., at least 10%, at least 20%, at least 25%, at least 30%, at least 40%, at least 50%, at least 60%, at least 70%, at least 75%, at least 80%, at least 90%, or at least 95%) during or after treatment, as compared to a control (e.g., a time point before or earlier in the treatment).

In addition, the peptides and compositions described herein can be used in methods for promoting healing of wounds that are not infected (or that show no evidence of infection). As described in the examples herein, for example, DRGN-1 increased keratinocyte migration into wound areas in in vitro studies, and accelerated skin wound closure and healing in in vivo studies. Thus, a peptide or composition containing one or more peptides described herein can be useful for treating a wound in a subject (e.g., a vertebrate such as a human), such that the wound has increased numbers of keratinocytes, shrinks in size more rapidly, and/or heals more quickly than it would without administration of the peptide or composition. In some embodiments, treatment of an uninfected wound with a peptide or composition can be considered effective if the wound size is reduced by at least 5% (e.g., at least 10%, at least 20%, at least 25%, at least 30%, at least 40%, at least 50%, at least 60%, at least 70%, at least 75%, at least 80%, at least 90%, or at least 95%) during or after treatment, as compared to a control (e.g., a time point before or earlier in the treatment).

The invention will be further described in the following examples, which do not limit the scope of the invention described in the claims.

EXAMPLES

Example 1

Materials and Methods

Bacterial strains and peptides: *Pseudomonas aeruginosa* ATCC 9027, *P. aeruginosa* PAO1 ATCC 15692, *Escherichia coli* O157:H7 ATCC 51659, and *Staphylococcus aureus* ATCC 25923 were obtained from the American Type Culture Collection (ATCC, Manassas, Va.). *Francisella novicida* U112 NR-13 was obtained from BEI Resources (Manassas, Va.). *P. aeruginosa* PAO1 cells that constitutively expressed GFP (PAO1 pTDK-GFP) and *S. aureus* SH1000 that expressed RFP (SH1000 pAH9-RFP) were provided by Dr. Douglas Weibel (Flickinger and Copeland, *J Am Chem Soc* 133:5966-5975, 2011) and Dr. Blaise Boles (Schwartz et al., *PLoS Pathog* 8, 2012, doi:10.1371/journal.ppat.1002744), respectively. DRGN-1 and VK25 were synthesized using conventional solid-phase methodology by ChinaPeptides (Suzhou, China). The crude compounds were purified to chromatographic homogeneity in the range of >95% by using reversed-phase high-performance liquid chromatography with a mass spectrometer by the company. LL-37 was purchased from AnaSpec (Fremont, Calif.). All peptides were reconstituted in a buffer consisting of 20 mg bovine serum albumin and 10 µl acetic acid in 50 ml phosphate buffered saline (PBS) (Fox et al., *Peptides* 33:197-205, 2012). Table 1 summarizes characteristics of peptides used in these studies.

Assays for antimicrobial and antibiofilm activity: *P. aeruginosa* and *S. aureus* were cultured in nutrient broth (NB) and mannitol-salt broth (MSB), *E. coli* was cultured in Luria broth (LB), and *F. novicida* was cultured in tryptic soy broth containing 0.1% cysteine (TSBC) overnight at 37° C. Overnight-cultured bacteria were numerated by a standard curve using optical density versus colony-forming units (CFU) per ml. The culture was resuspended in 10 mM sodium phosphate buffer (pH 7.4) and adjusted to a final amount of $2\times10^6$ CFU/ml. For $EC_{50}$ determination, peptides were used at variable concentrations (0.1-100 µg/ml) from a stock solution. Fifty µl of each concentration of peptide solution was added to each corresponding well of a 96-well plate (BD Falcon, Franklin Lakes, N.J.) and 50 µl of bacteria was added and incubated for 3 hours at 37° C. After dilution in the buffer, the bacteria were spotted on an agar plate of the corresponding media and colonies were numerated. Antibiofilm activity was measured as described elsewhere (Durham-Colleran et al., *Microb Ecol* 59:457-465, 2010) with the following modifications. Two-fold diluted peptides in TSB medium were incubated with bacteria (1:50 dilution in the same medium) overnight. A crystal violet assay was used for biofilm formation as described elsewhere (Sepanović et al., *J Microbiol Methods* 40:175-179, 2000). For confocal microscopy, bacteria (*P. aeruginosa* PAO1 pTDK-GFP and *S. aureus* SH1000 pAH9-RFP) were grown on the Lab-Tek II chamber slide (Thermo Scientific, Waltham, Mass.) for 24 hours, and biofilms attached to the glass were observed with a 40× objective using a Nikon TE2000-U confocal laser scanning microscope equipped with an argon ion laser.

Cell infection: Adult human epidermal keratinocytes HEKa (Invitrogen, Carlsbad, Calif.) cells were seeded in 24-well plates (Corning) and grown until they reached confluence (48 h) in EpiLife medium (Thermo Scientific) supplemented with human keratinocyte growth supplements (HKGS) containing 0.2% v/v bovine pituitary extract, 5 µg/ml bovine insulin, 0.18 µg/ml hydrocortisone, 5 µg/ml bovine transferrin, and 0.2 ng/ml human epidermal growth factor (EGF) (Invitrogen). The bacterial strain *P. aeruginosa* ATCC 9027 was grown in brain heart infusion (BHI) media at 37° C. with mild shaking and then harvested by centrifugation. Bacterial suspension (MOI 10) in EpiLife medium was co-incubated with keratinocytes for 2 hours at 37° C. and 5% $CO_2$. The medium was aspirated and the cells were washed three times with PBS to remove non-adherent bacteria. In order to kill extracellular bacteria, cells were incubated for 1 hour in EpiLife without HKGS supplemented with 100 µg/ml of gentamicin. The medium was then aspirated and the infected cells were washed three times, as described above. Three hundred microliters of peptide solution (30 µg/ml) in EpiLife without HKGS was added to each well and the plate was incubated for 2 hours at 37° C. and 5% $CO_2$. Then, the peptide solution was removed and the cells were washed again with PBS three times and lysed with 100 µl of 0.1% Triton X-100 in PBS for 5 minutes at room temperature. The resulting bacterial suspension was sonicated in a water bath for 10 minutes to break up possible clumps, and appropriate dilutions were plated on agar plates for colony counts. The CFU were counted after 24 hours at 37° C.

Membrane permeability: For intrinsic permeabilization of bacterial membrane, ethidium bromide (EtBr) uptake was in performed 10 mM potassium phosphate buffer (pH 7.2) as described (Zou et al., *J Bacteriol* 194:413-425, 2012) with some modifications. Overnight cultures of *P. aeruginosa* ATCC 9027 in BHI were transferred to fresh medium and grown to $OD_{600}$ values of 0.5-0.6 (log phase). Cells were harvested and resuspended in 10 mM potassium phosphate buffer (pH 7.2) at a final $OD_{600}$ of 0.12-0.15. The cells (40 µl) were added to 50 µl of 12 µM EtBr, followed by the peptide (20 µg/ml final) samples after 30 seconds. Excitation and emission wavelengths were set at 545 nm and 600 nm, respectively. The increase in fluorescence as a result of partitioning of EtBr into the cytosol was measured 20 minutes after the addition of peptides using a fluorescence spectrophotometer (Tecan Safire$^2$ Multi-detection Microplate Reader; Tecan Group Ltd., Männedorf, Switzerland). Membrane potential was measured by $DiSC_3(5)$ as described elsewhere (Rodriguez et al., *Front Chem* 2:1-12, 2014). Briefly, mid-log phase bacteria were suspended in 5 mM HEPES containing 20 mM glucose (OD=0.05) and $DiSC_3(5)$ (1 µM final) was added for 1 hour at room temperature. KCl was then added at 0.1 M of final concentration. After addition with peptide (20 µg/ml) or TX-100 (final 0.1%), fluorescence was excited at 622 nm (bandwidth 5 nm) and monitored at 670 nm for emission (bandwidth 20 nm).

Peptide-DNA binding assays: Gel-retardation experiments were performed using a method described elsewhere (Park et al., *Biochem Biophys Res Commun* 244:253-257, 1998). Briefly, 100 ng of plasmid DNA (pTrcHis-LTA4H) was incubated with increasing concentrations of peptides in 20 µl of binding buffer [5% glycerol, 10 mM Tris-HCl (pH 8.0), 1 mM EDTA, 1 mM DTT, 20 mM KCl and 50 µg/ml BSA] at room temperature for 20 minutes and then subjected to electrophoresis on a 1.0% agarose gel. DNA bands were visualized by EtBr staining. The peptide-to-DNA weight ratios were 0:1, 0.63:1, 1.25:1, 2.5:1, 5:1, 10:1, 20:1 and 40:1, respectively.

Circular dichroism (CD) analysis: CD spectra of the peptides were collected using a Jasco J-1500 spectropolarimeter. Data was collected in a 0.1 cm path length cuvette, with a chamber temperature of 25° C. Spectra were collected from 190 to 260 nm using 0.1-nm intervals. Three scans per sample were averaged. All peptides were analyzed at 100 µg/ml concentration in three different media: 10 mM sodium phosphate (pH 7), 50% (v/v) trifluoroethanol (TFE) in 10 mM sodium phosphate (pH 7), and 60 mM sodium dodecyl sulfate (SDS) in 10 mM sodium phosphate (pH 7).

In vitro scratch wound closure assays: In vitro wound closure was assayed in confluent cell monolayers of HEKa (Invitrogen) as described elsewhere (Kim et al., *Amino Acids* 46:2333-2343, 2014). Cells were seeded in 6-well plates (Corning, N.Y., USA) and grown until they reached confluence (48 hours) in EpiLife medium supplemented with HKGS. Cells were starved for 18 hours in EpiLife without HKGS and then scratched once vertically with a 200-µl pipette tip to create an artificial wound. For inhibitor studies, mitomycin C (20 µM final) and AG1478 (0.2 µM final) were added 90 minutes and 10 minutes prior to scratch generation. After being washed twice with PBS to remove cellular debris, cells were treated with DRGN-1, VK25 or LL-37. PBS was used as a negative control. Cells were photographed before peptide treatment and 7 hours and 24 hours after peptide treatment using an EVOS® Cell Imaging Systems (Invitrogen). The same image fields were captured and the wound areas were estimated using ImageJ software (Schneider et al., *Nat Methods* 9:671-675, 2012).

MTT assay: The toxic effect of the peptides on adult human epidermal keratinocytes (HEKa) cells was evaluated using the MTT (3-(4,5-dimethylthiazolyl-2)-2,5-diphenyltetrazolium bromide) colorimetric method (Di Grazia et al., *Antimicrob Agents Chemother* 58:2520-2527, 2014). The color intensity of the MTT is directly proportional to the number of metabolically active cells. Keratinocytes were plated in triplicate wells of a 96-well plate, at $4 \times 10^4$ cells/well in EpiLife medium supplemented with HKGS. After overnight incubation at 37° C. in a 5% $CO_2$ atmosphere, the plate was incubated with the peptides at different concentrations for 2 hours, and 0.5 mg/ml of MTT was added. After 4 hours of incubation, formazan crystals were dissolved by adding 100 µl of acidified isopropanol, and the absorbance of each well was measured at 570 nm using a microplate reader (PowerWave X; BioTek, Winooski, Vt.).

Western blotting: Semifluent HEKa cells were serum-starved for 3 hours and then stimulated with 10 µg/ml DRGN-1 or HKGS for 5-30 minutes at 37° C. AG1478 (0.2 µM final) was added 10 minutes prior to DRGN-1 or HKGS treatment. Cells were lysed with 2×Laemmli sample buffer (Bio-Rad; Hercules, Calif.) containing 5 mM sodium fluoride and 2 mM sodium vanadate. Cell lysates were separated on a 4-12% SDS-PAGE gel and transferred to polyvinylidene difluoride membrane using an iBlot system (Invitrogen). The membranes were probed with antibodies specific to phospho-EGFR and EGFR (Cell Signaling). The membranes were then treated with horseradish peroxidase-conjugated donkey anti-rabbit IgG (Abcam; Cambridge, UK) and developed by SuperSignal West Femto Chemiluminescent Substrate (ThermoFisher Scientific; Waltham, Mass.) under GelDoc Imaging System (Bio-Rad).

Animal model of wound healing: Female BALB/c mice (12 weeks old) were purchased from Jackson Laboratory (Bar Harbor, Me.). Mice were anesthetized with isoflurane and the dorsal skin was shaved to remove hair. The next day, a superficial wound was created between the shoulder blades of the mice using a 6 mm biopsy punch. The wounds were topically treated with 20 µl containing 20 µg DRGN-1 or VK25 in 1% hypromellose every 48 h (n=5 animals per group) and covered with a Tegaderm-type semi occlusive dressing (3M; St. Paul, Minn.) attached to a silicone disc (0.5 mm thick, Life Technologies) by Mastisol liquid (Eloquest Healthcare). Each wound site was digitally photographed at the indicated time intervals and wound areas were determined on photographs using ImageJ. Changes in the wound areas over time were expressed as the percentage of the original wound areas.

For infected wounds, *P. aeruginosa* ATCC 9027 and *S. aureus* ATCC 25923 were mixed and grown on 6 mm polycarbonate filter on Nutrient agar plates overnight Dean et al., *Biofouling* 31:151-161, 2015). The resulting biofilm was applied to the biopsy wound and covered with a Tegaderm dressing adhered to the skin with Mastisol liquid. Mice were housed individually with ad libitum rodent chow and water for two days. The wounds (5 mice per group) were topically treated with 20 µl containing 20 µg peptide with 1% hypromellose in 10 mM phosphate buffer every two days until six days after the first treatment. Each wound site was then digitally photographed at the indicated time intervals, and wound areas were determined on photographs using ImageJ software. Changes in wound areas over time were expressed as the percentage of the original wound areas. To assess bacterial colonization, wounds were harvested at day 6 post treatment and homogenized in PBS. Mannitol salt agar was used to selectively culture *S. aureus* and tryptic soy agar with triclosan or centrimide agar was used to selectively culture *P. aeruginosa*. At day 11 post treatment, all mice were sacrificed and tissue samples were harvested in a 4% paraformaldehyde solution. The sections of fixed skin were stained with hematoxylin and eosin (H&E) for further histological analysis by AML Laboratories (Baltimore, Md.).

Statistical analysis: P-values were calculated by one-way ANOVA or Student's t-test. Statistical significance was set at P<0.05. Data are presented as arithmetic mean±SD. Each experiment was repeated at least three times independently.

Example 2

Antimicrobial and Anti-Biofilm Activity of DRGN-1

Figure 2A:
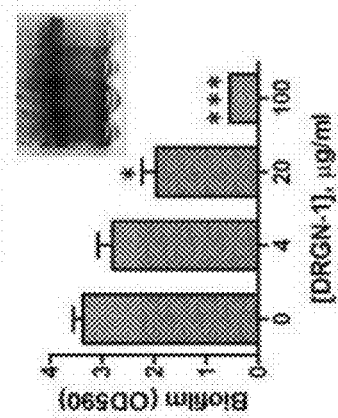
FIGS. 2A-2C demonstrate the antibiofilm activity of DRGN-1.
Figure 2B:
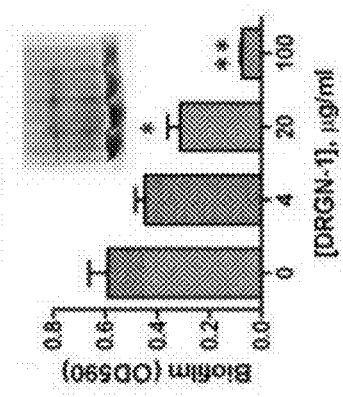
Figure 2C:
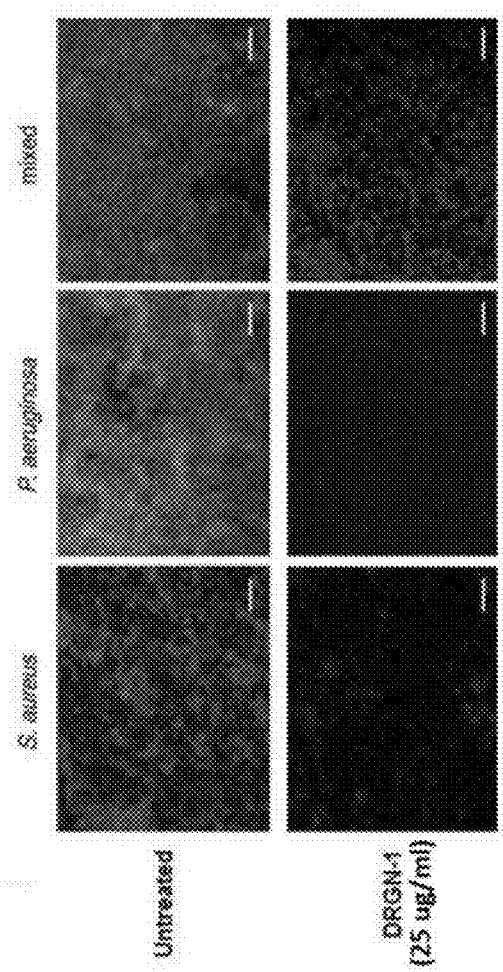

To investigate whether DRGN-1 and VK25 could exert antimicrobial effects, the activity of CAMPs was tested against the Gram-negative *P. aeruginosa*, *F. novicida*, and *E. coli*, and the Gram-positive *S. aureus*. The results showed that DRGN-1 was indeed antimicrobial in an $EC_{50}$ assay against the Gram-negative *P. aeruginosa* and *E. coli* and the Gram-positive *S. aureus*, with a range of 0.77-7.1 µg/ml (0.50-4.62 µM), while VK25 was ineffective within 100 µg/ml (TABLE 2). This implied that switching the proline-serine sequence to serine-proline may have contributed to the peptide's antimicrobial activity. It is of note that the peptides displayed activities comparable to that of the "classic" AMP human cathelicidin LL-37 ($EC_{50}$=0.24-2.7 µg/ml; 0.05-0.60 µM). Next, the ability of DRGN-1 to prevent the formation of biofilm after 18 hours was examined by crystal violet staining and confocal microscopy (FIG. 1). When cultured in a polystyrene tube under shaking conditions, *P. aeruginosa* and *S. aureus* formed biofilms along the side wall of tube. The biofilms were inhibited by DRGN-1 in a concentration-dependent manner (FIGS. 2A and 2B). For confocal imaging, DRGN-1 (final concentration, 25 µg/ml) was incubated with bacteria overnight in the wells of a chamber slide. The next day, the wells were rinsed and the development of a biofilm was compared with a control well (without DRGN-1). *P. aeruginosa* GFP+ and *S. aureus* RFP+ were used for these studies. The cells were incubated for 24 hours in TSB medium in the presence of DRGN-1. Biofilms of both *P. aeruginosa* and *S. aureus* were significantly reduced by DRGN-1. In the 24 hour control of mixed-culture biofilms, *P. aeruginosa* overgrew *S. aureus* in 99:1 ratio. Treatment with DRGN-1 had a significant inhibitory effect on the mixed cultures in contrast with untreated control.

Example 3

Activity on *P. aeruginosa*-infected HEKa keratinocytes

Figure 4:
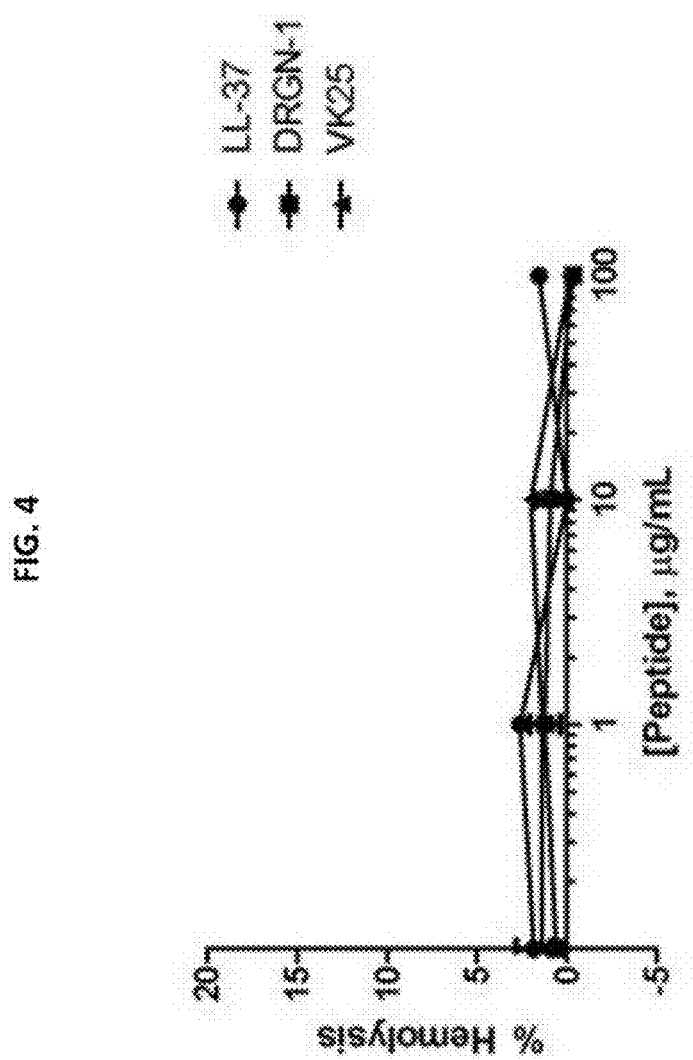
FIG. 4 is a graph plotting hemolytic activity of CAMPs. A fresh sheep erythrocyte suspension was incubated with the indicated peptides. Hemoglobin release into the supernatant was measured by absorbance at 567 nm to indicate membrane damage of erythrocytes.

To gain insight into the activity of DRGN-1 against internalized *P. aeruginosa*, HEKa keratinocytes were infected with *P. aeruginosa* ATCC 9027 and subsequently treated with DRGN-1 and VK25. As highlighted in FIG. 3, the killing of infected keratinocytes became more pronounced 2 hours after their exposure to the bacteria, presumably due to *P. aeruginosa*-induced apoptotic cell death, which was strongly prevented by treatment with DRGN-1 (FIGS. 3A-3D). DRGN-1, but not VK25, significantly reduced the number of internalized bacteria, with the peptide causing 36% killing of the bacteria at the concentration used (30 µg/ml) and after 2 hours (FIG. 3E). The effect of DRGN-1 and VK25 on the survival of metabolically active HEKa cells was further studied using an MTT-based assay. As shown in FIG. 3F, both DRGN-1 and VK25 were devoid of toxic effects at a concentration range of 12.5~100 µg/ml. However, the control CAMP LL-37 caused a significant decrease in HEKa cell viability at concentrations ranging from 50~100 µg/ml (FIG. 3F). DRGN-1 did not show any toxicity against erythrocytes in a high concentration (FIG. 4).

Example 4

Effects of DRGN-1 on Membrane Permeability and DNA Binding

The permeabilization of *P. aeruginosa* ATCC 9027 by CAMPs was assessed by measuring the uptake of the fluorescent probe EtBr, a dye that fluoresces upon entering the cell. EtBr will not fluoresce unless it permeates both the inner and outer membranes and intercalates into nucleic acid. The uptake of EtBr was significantly higher in the presence of DRGN-1 or LL-37 than in the presence of VK25 or the untreated control (FIG. 5A). The effect of CAMPs on the membrane potential was measured by monitoring the membrane potential using the fluorescent dye $DiSC_3(5)$ (FIG. 5B). $DiSC_3(5)$ is taken up by bacterial cells according to the magnitude of the electrical potential gradient ($\Delta\Psi$) of the cytoplasmic membrane, and becomes concentrated in the cytoplasmic membrane, where it self-quenches its own fluorescence. Any compound that permeabilizes the cytoplasmic membrane, and thus depolarizes the $\Delta\Psi$, will lead to the release of $DiSC_3(5)$ and a consequent increase in fluorescence. CAMPs were tested against *P. aeruginosa* ATCC 9027 at concentration of 20 µg/ml, which was expected to cause a large and immediate increase in fluorescence (indicative of loss of membrane potential). DRGN-1 showed a smaller effect (~10% relative to Triton X-100 served as a positive control), while VK25 did not have any effect. These results suggested that in addition to membrane disruption, DRGN-1, but not VK25, permeabilizes the membrane and slightly depolarizes the membrane potential.

In an attempt to identify the molecular mechanism of action, the DNA binding activity of the CAMPs was examined by analyzing the electrophoretic mobility of DNA bands at various weight ratios of peptides to DNA on an agarose gel (FIG. 5C). DRGN-1 and LL-37 inhibited DNA migration above weight ratios of 5.0 and 2.5, respectively. In contrast, VK25 suppressed DNA migration above a weight ratio of 40. This result indicated that DRGN-1 binds to DNA at least 8 times more tightly than VK25.

Example 5

Structure Analysis of DRGN-1 by CD

The reversal of two N-terminal amino acids (Ser-Pro) in a histone H1-derived peptide of *V. komodoensis* caused drastic changes in antimicrobial activity, antibiofilm activity, membrane permeability, and DNA binding. Therefore, experiments were conducted to determine the secondary structure of the peptides in the membrane-mimicking media, SDS and TFE (FIGS. 6A-6D). DRGN-1 and VK25 showed a random coil conformation in aqueous solution (10 mM phosphate buffer) and 60 mM SDS solution. The α-helical contents of DRGN-1 and VK25 were 22.3 and 32.8% in 50% TFE, respectively. Both DRGN-1 and VK25 had a very low hydrophobic moment (0.013 and 0.088, respectively) compared with that of the highly α-helical LL-37 (0.521), suggesting that DRGN-1 and VK25 are not α-helical (TABLE 1). Nevertheless, DRGN-1 (0.64) displayed a slightly larger R2 value, the hallmark of the coiled-coil α-helical structure in 50% TFE, than VK25 (0.44). These results suggested that the reversal of amino acids at the N-terminal results in an overall conformational change.

Example 6

Effects of DRGN-1 on in Vitro Wound Closure

Figure 7A:
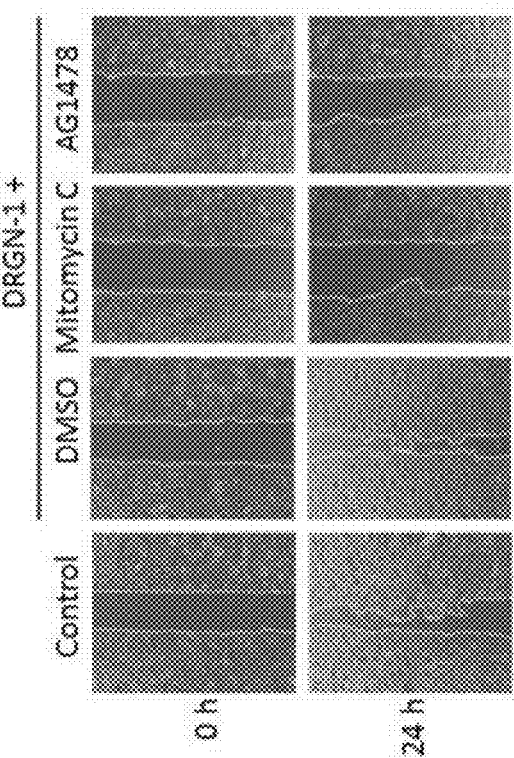
FIGS. 7A-7D show results of wound-healing ("scratch") assays using HEKa cells.
Figure 7B:
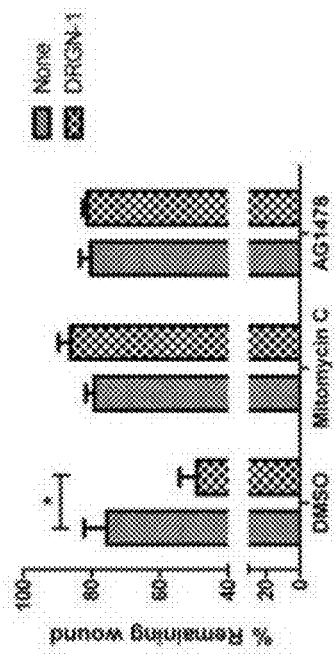
Figure 7C:
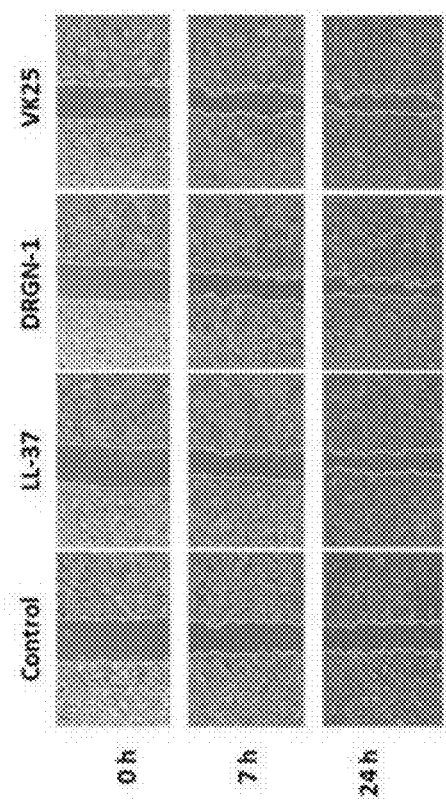
Figure 7D:
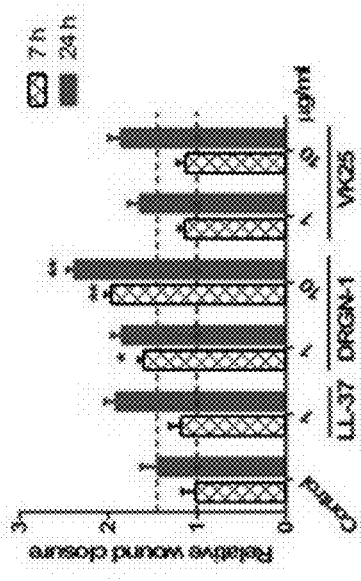

A potential function of CAMPs is the activation of keratinocyte migration, resulting in skin wound healing (Kim et al., *Amino Acids* 46:2333-2343, 2014; Yin et al., *Invest Ophthalmol Vis Sci* 51:1891-1897, 2010; and Steinstraesser et al., *PLoS One* 7:e39373, 2012). The capacity of DRGN-1 to induce wound closure was therefore tested. Initial studies were conducted to investigate whether CAMPs induced migration of HEKa cells into wound area using a scratch wound closure assay. The migration of cells into the wounded area was significantly increased in the presence of DRGN-1 and LL-37 (1 µg or 10 µg per ml) over migration in the control within 7 hours and 24 hours after wounding (FIGS. 7A and 7B). There was minimal, non-significant wound closure activity in the presence of VK25, comparable to the control treatment (peptide reconstitution buffer). Afterward, to determine whether the wound closure was influenced by an increased proliferation of keratinocytes upon their exposure to DRGN-1, the wound healing assay was carried out in the presence of 20 µM mitomycin C to block cell proliferation. As shown in FIGS. 7C and 7D, mitomycin C strongly inhibited the migratory activity of keratinocytes induced by 10 µg/ml DRGN-1. This suggested that proliferation of HEKa cells highly contributes to the wound-healing effect produced by DRGN-1. To further understand the receptor pathway by which DRGN-1 activates keratinocyte migration and proliferation, a G-protein-coupled receptor, EGFR, was selected as a possible DRGN-1 receptor, because it has been reported to regulate keratinocyte migration and proliferation (Yin et al., supra; Minder et al., *J Biol Chem* 287:35201-35211, 2012; and Niyonsaba et al., *J Invest Dermatol* 127:594-604, 2007). AG1478 is an inhibitor of EGFR tyrosine kinase, which blocks the activation of EGFR (Hoq et al., *J Dermatol Sci* 64:108-118, 2011; and Tokumaru et al., *J Immunol* 175: 4662-4668, 2005). Interestingly, pretreatment of HEKa cells with 0.2 µM AG1478 prevented cell migration induced by DRGN-1. To examine EGFR transactivation by DRGN-1, EGFR phosphorylation was investigated by Western blotting with and anti-phospho-EGFR antibody. DRGN-1 phosphorylated EGFR at 5 minutes, and the phosphorylation persisted for 20 minutes, which was not observed in AG1478-treated cells (FIGS. 8A-8C). The amount of EGFR protein did not change during this time period, and treatment with HKGS containing 0.2 ng/ml of human EGF was used as a positive control. EGFR signaling pathway initiates several signal transduction cascades, such as STAT3 and Akt with the functional consequence of enhanced cell migration (Andl et al., *Am J Physiol Gastrointest Liver Physiol* 287: G1227-G1237, 2004). STAT3 was also phosphorylated 10-30 minutes after the addition of DRGN-1 (FIGS. 8D-8F).

From these results, it was concluded that DRGN-1-induced keratinocyte migration occurs via EGFR-STAT3 transactivation.

Example 7

Efficacy of DRGN-1 on in Vivo Wound Healing

To evaluate the potential clinical application of DRGN-1, the in vivo wound closure activity of DRGN-1 was first investigated in a mouse full-thickness skin wound model. Full-thickness round wounds of 6 mm in diameter were made between the shoulder blades, and the wound closure was evaluated by measurement of original wound area (%). When DRGN-1 or VK25 (20 µg/wound) was applied topically every 2 days post-injury, DRGN-1-treated wounds were consistently smaller than wounds treated with PBS or VK25 (FIGS. 9A-9C). At day 6, wounds treated with DRGN-1 were smaller in area (41% compared to original wound area) than the control (65%) or VK25-treated (85%) wound. These results indicated that DRGN-1 accelerates skin wound closure and healing in mice.

Figure 10A:
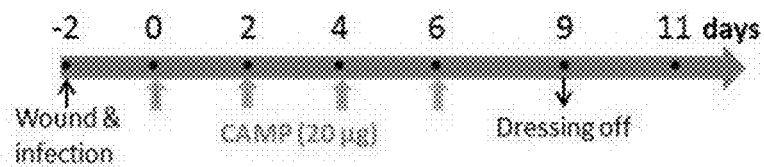
FIGS. 10A-10D show the wound healing efficiency of peptides in a mixed biofilm-infected mouse skin wound model.
Figure 10B:
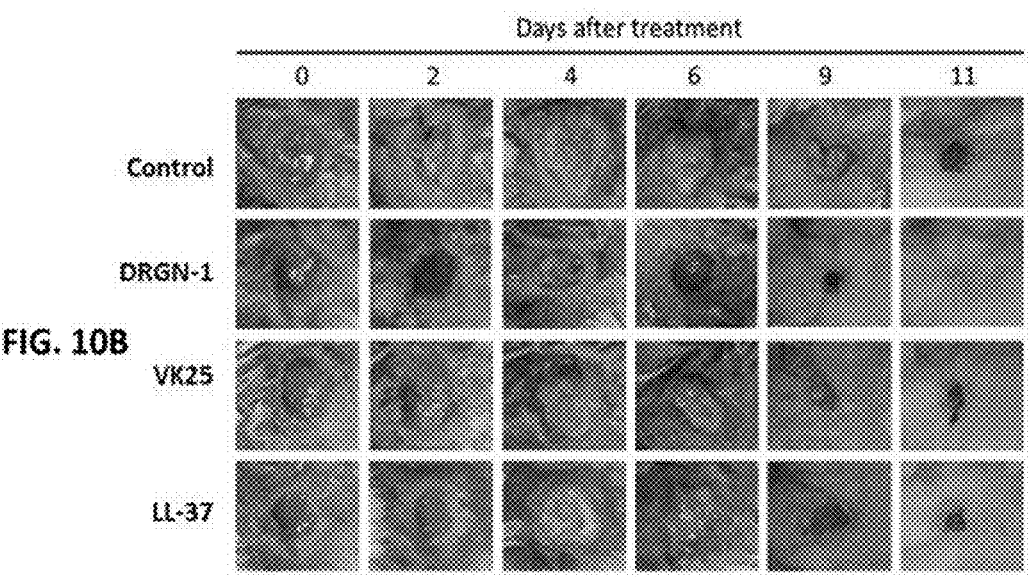
Figure 10C:
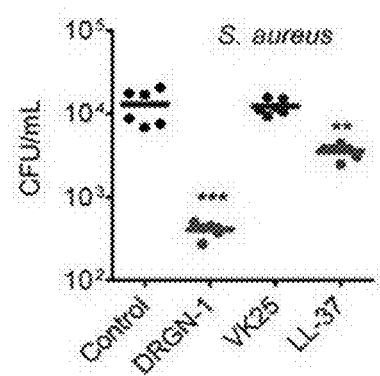
Figure 10D:
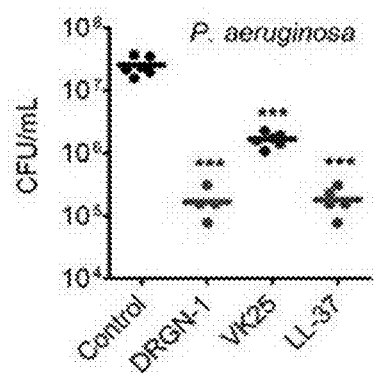
Figure 11:
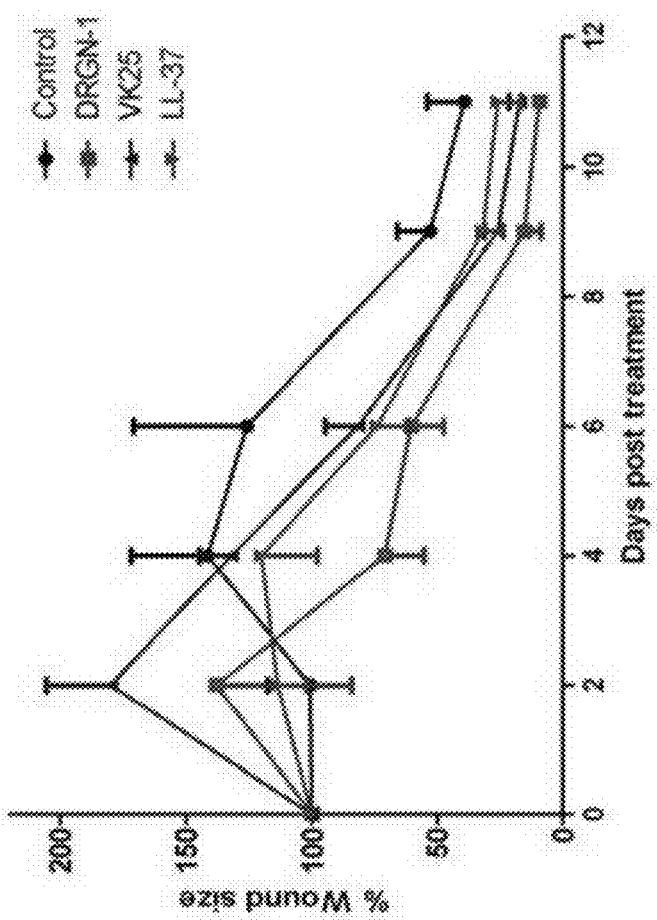
FIG. 11 is a graph plotting changes in the percentage of wound area at each time point in comparison to the original wound area. Wound area was determined from photographs of a mouse skin wound model using ImageJ. *P<0.05 and **P<0.01.
Figure 12:
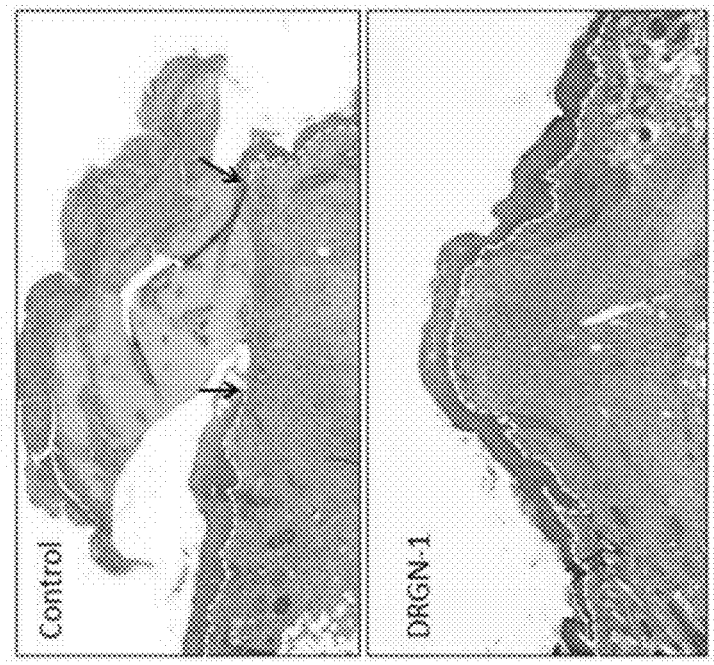
FIG. 12 is a pair of pictures showing histologic analysis of P. aeruginosa/S. aureus-infected wounds that were untreated (top) or treated with DRGN-1 (bottom). Sections from wound tissue samples harvested on day 11 after treatment were stained with hematoxylin and eosin. Black arrows indicate epidermal gaps, which determine the degree of wound closure. Dermo-epidermal boundaries are outlined by dashed lines.

Chronic wounds most often are infected with multiple bacteria (polymicrobial) that produce a large amount of biofilm as part of the pathology of infection, which makes such wounds difficult to treat. In addition, these infections can be caused by antibiotic-resistant organisms, which require the development of new therapies. In this study, a mouse model was developed to evaluate the use of candidate peptides previously determined to have broad-spectrum antimicrobial and antibiofilm properties as topical therapeutics for infected wounds. Using this model, the potential clinical application of DRGN-1 against *P. aeruginosa/S. aureus* biofilm-infected wounds was evaluated (FIG. 10A). Full-thickness round wounds 6 mm in diameter were made between the shoulder blades of the mice, and were overlaid with a mixed biofilm of *P. aeruginosa/S. aureus* grown on agar for 2 days. The kinetics of wound closure was evaluated by measuring the original wound area before and after treatment with peptides. DRGN-1, VK25, and LL-37 (20 µg/wound) were applied topically to their specified groups every other day until day 6. Reconstitution buffer was used as a control in this experiment. Wounds treated with DRGN-1 were consistently smaller than wounds treated with buffer control, VK25, or LL-37 (FIGS. 10B and 11). The difference in size was apparent by day 4 after the first treatment. By day 11, the wounds treated with DRGN-1 were completely healed, while the wounds treated with PBS, VK25, and LL-37 were not. After 6 days of the first treatment (3 treatments), the bacterial counts of *S. aureus* and *P. aeruginosa* were significantly reduced in the DRGN-1 and LL-37-treated groups compared to the control group (FIGS. 10C and 10D). In contrast, there was no significant reduction in *S. aureus*, and only a slight reduction in *P. aeruginosa* in VK25-applied wound areas. These results indicated that DRGN-1 accelerates skin wound closure and healing in *P. aeruginosa/S. aureus* biofilm-infected mice. When the wound dressings were taken off on day 6, wound healing was accelerated in both treated and untreated conditions due to the air exposure, as observed at day 9 and 11 post treatment. In addition, hematoxylin-eosin staining of skin at day 11 clearly demonstrated that the skin layers were completely rehabilitated in the DRGN-1-treated wounds (FIG. 12).

TABLE 1

Summary of CAMPs used in this study.

| CAMP | Sequence (SEQ ID NO:) | Net charge | Hydrophobicity (H)* | Hydrophobic moment (µH)* | MW | AMP probability (SVM)** |
|---|---|---|---|---|---|---|
| DRGN-1 | PSKKTKPVKPKKVA (SEQ ID NO: 2) | +6 | −0.058 | 0.013 | 1535.95 | 0.866 |
| VK25 | SPKKTKPVKPKKVA (SEQ ID NO: 1) | +6 | −0.058 | 0.088 | 1535.95 | 0.866 |
| LL-37 | LLGDFFRKSKEKIGKEFKRIVQRIKDFLRNLVPRTES (SEQ ID NO: 3) | +6 | 0.201 | 0.521 | 4493.3 | 0.762 |

*Physicochemical parameter (hydrophobicity and hydrophobic moment) were calculated by HeliQuest, a web server to screen sequences with specific alpha-helical properties (Gautier et al., Bioinformatics 24:2101-2102, 2008).
**AMP probability was predicted by a web-based prediction tool CAMP (camp.bicnir-rh.res.in/predict/) using support vector machine (SVM) algorithm.

TABLE 2

Antimicrobial activity of DRGN-1, VK25 and LL-37 against Gram-positive and Gram-negative bacteria.

| | DRGN-1 | | VK25 | LL-37 | |
|---|---|---|---|---|---|
| Species | $EC_{50}$ | 95% CI | $EC_{50}$ | $EC_{50}$ | 95% CI |
| P. aeruginosa PAO1 | 6.85 | 4.22-11.1 | >100 | ND | — |
| P. aeruginosa ATCC 9027 | 4.39 | 1.12-17.1 | >100 | 1.08 | 0.77-1.5 |
| P. aeruginosa PAO1 (pTDK-GFP) | 7.10 | 3.46-14.6 | >100 | 2.69 | 1.32-5.5 |
| F. novicida U112 | >100 | — | >100 | 0.24* | 0.18-0.3 |
| E. coli O157:H7 | 3.48 | (very wide) | >100 | ND | — |
| S. aureus ATCC25923 | 4.04 | (very wide) | >100 | 1.27¶ | 0.44-3.7 |
| S. aureus SH1000 (pAH9-RFP) | 0.77 | 0.25-2. | >100 | ND | — |

This table indicates the $EC_{50}$ (µg/ml) and 95% confidence interval (CI) of the peptides against P. aeruginosa and S. aureus in an anti-microbial assay.
*and ¶; see, Amer et al., Biochem Biophys Res Commun 396: 246-251, 2010; and Dean et al., BMC Microbiol 11: 114, 2011, respectively.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified peptide having a length of 13 to 15 amino acids, the peptide comprising:
   (a) the amino acid sequence set forth in SEQ ID NO:2; or
   (b) the amino acid sequence set forth in SEQ ID NO:2 with one substitution, addition, or deletion.

2. The purified peptide of claim 1, wherein the peptide comprises the amino acid sequence set forth in SEQ ID NO:2.

3. The purified peptide of claim 1, wherein the peptide comprises the amino acid sequence set forth in SEQ ID NO:2 with one substitution, addition, or deletion.

4. A composition comprising the peptide of claim 1 and an excipient.

5. An article of manufacture comprising the purified peptide of claim 1.

6. A method for treating an infection by a microbial organism, comprising contacting the microbial organism with a composition comprising the peptide of claim 1 and an excipient.

7. The method of claim 6, wherein the composition comprises about 0.01 µg/ml to about 10 µg/ml peptide.

8. The method of claim 6, wherein after the contacting, growth of the microbial organism is reduced by at least about 25 percent when measured in an assay to measure colony formation.

9. The method of claim 6, wherein the composition further comprises a second purified peptide having a length of 10 to 12 amino acids, the second purified peptide comprising the amino acid sequence set forth in SEQ ID NO:4 or the amino acid sequence set forth in SEQ ID NO:4 with one substitution, addition, or deletion.

10. A method for inhibiting the growth of a biofilm on a surface, comprising contacting the surface with a composition comprising the peptide of claim 1 and an excipient.

11. The method of claim 10, wherein the surface is on a prosthetic or an implant.

12. The method of claim 10, wherein after the contacting, growth of the biofilm is reduced by at least about 5 percent, compared to a control, when measured in an assay to measure optical density.

13. The method of claim 10, wherein the composition further comprises a second purified peptide having a length of 10 to 12 amino acids, the second purified peptide comprising the amino acid sequence set forth in SEQ ID NO:4 or the amino acid sequence set forth in SEQ ID NO:4 with one substitution, addition, or deletion.

14. A method for treating an infection in a subject in need thereof, comprising:
   determining that the subject is resistant to one or more conventional antibiotics, or is suspected of being resistant to one or more conventional antibiotics; and
   treating the subject with the composition of claim 4.

15. A method for improving the effectiveness of treatment for a microbial infection in a subject in need thereof, comprising:
   (a) administering to the subject (i) an amount of the peptide of claim 1 that is sub-anti-microbial but is effective to reduce biofilm levels or inhibit biofilm formation, or (ii) the peptide of claim 1 under conditions that are sub-anti-microbial but are effective to reduce biofilm levels or inhibit biofilm formation; and subsequently
   (b) administering to the subject (i) an anti-microbial amount of the peptide, or (ii) the peptide under conditions that are anti-microbial, or (iii) one or more conventional antibiotics.

16. The method of claim 15, wherein in step (a), the peptide is administered under high salt conditions.

17. The method of claim 16, wherein the high salt conditions comprise 125 to 150 mM salt.

18. A method for promoting wound healing in a subject, comprising administering to the subject a composition comprising the peptide of claim 1 and an excipient.

19. The method of claim 18, wherein the composition comprises about 0.01 µg/ml to about 10 µg/ml peptide.

20. The method of claim 18, wherein the composition further comprises a second purified peptide having a length of 10 to 12 amino acids, the second purified peptide comprising the amino acid sequence set forth in SEQ ID NO:4 or the amino acid sequence set forth in SEQ ID NO:4 with one substitution, addition, or deletion.

* * * * *